US011427836B2

(12) United States Patent
Mingozzi et al.

(10) Patent No.: US 11,427,836 B2
(45) Date of Patent: Aug. 30, 2022

(54) METHOD FOR REDUCING THE EXPRESSION OF NKCC1 IN A SUBJECT

(71) Applicants: INSERM (INSTITUT NATIONAL DE LA SANTÉ ET DE LA RECHERCHE MÉDICALE), Paris (FR); UNIVERSITÉ D'EVRY-VAL-D'ESSONNE, Evry (FR); GENETHON, Evry (FR); FONDAZIONE ISTITUTO ITALIANO DI TECNOLOGIA, Genoa (IT); FONDAZIONE TELETHON, Rome (IT)

(72) Inventors: Federico Mingozzi, Paris (FR); Giuseppe Ronzitti, Paris (FR); Andrea Contestabile, Genoa (IT); Laura Cancedda, Genoa (IT)

(73) Assignees: INSERM (INSTITUT NATIONAL DE LA SANTÉ ET DE LA RECHERCHE MÉDICALE, Paris (FR); UNIVERSITE D'EVRY-VAL-D'ESSONNE, Evry (FR); GENETHON, Evry (FR); FONDAZIONE ISTITUTO ITALIANO DI TECNOLOGIA, Genoa (IT); FONDAZIONE TELETHON, Rome (IT)

( * ) Notice: Subject to any disclaimer, the term of this patent is extended or adjusted under 35 U.S.C. 154(b) by 139 days.

(21) Appl. No.: 16/604,648

(22) PCT Filed: Apr. 11, 2018

(86) PCT No.: PCT/EP2018/059255
§ 371 (c)(1),
(2) Date: Oct. 11, 2019

(87) PCT Pub. No.: WO2018/189225
PCT Pub. Date: Oct. 18, 2018

(65) Prior Publication Data
US 2021/0130847 A1 May 6, 2021

(30) Foreign Application Priority Data
Apr. 11, 2017 (EP) .................. 17305434

(51) Int. Cl.
C12N 15/113 (2010.01)
C12N 15/86 (2006.01)
A61K 45/06 (2006.01)
C12Q 1/68 (2018.01)

(52) U.S. Cl.
CPC .............. *C12N 15/86* (2013.01); *A61K 45/06* (2013.01); *C12N 15/113* (2013.01); *C12N 2310/141* (2013.01); *C12N 2310/531* (2013.01)

(58) Field of Classification Search
None
See application file for complete search history.

(56) References Cited

U.S. PATENT DOCUMENTS

| 5,994,136 | A | 11/1999 | Naldini et al. |
| 6,013,516 | A | 1/2000 | Verma |
| 6,156,303 | A | 12/2000 | Russell et al. |
| 2004/0053876 | A1 | 3/2004 | Turner et al. |
| 2004/0265230 | A1 | 12/2004 | Martinez et al. |

FOREIGN PATENT DOCUMENTS

| EP | 2808391 A1 | 12/2014 |
| WO | 9811244 A2 | 3/1998 |
| WO | 9961601 A2 | 12/1999 |
| WO | 0028061 A2 | 5/2000 |
| WO | 2015091857 A1 | 6/2015 |
| WO | 2016190899 A1 | 12/2016 |

OTHER PUBLICATIONS

Agarwal et al; "Predicting effective microRNA target sites in mammalian mRNAs"; eLife; Aug. 12, 2015; e05005. DOI: 10.7554/eLife.05005; pp. 1-38.
Andersen et al; "Herpesvirus-Mediated Gene Delivery into the Rat Brain: Specificity and Efficiency of the Neuron-Specific Enolase Promoter"; Cellular and Molecular Neurobiology, vol. 13, Issue No. 5; 1993; pp. 503-515.
Bantel-Schaal et al; "Human Adero-Associated Virus Type 5 is Only Distantly Related to Other Known Primate Helper-Dependent Parvoviruses"; Journal of Virology, vol. 73, Issue No. 2; 1999; pp. 939-947.
Ben-Ari et al; "Failure of the Nemo Trial: Burmetanide is a Promising Agent to Treat Many Brain Disorders but Not Newborn Seizures"; Frontiers in Cellular Neuroscience, vol. 10, Article 90; 2016; pp. 1-6.
Boshart et al; "A Very Strong Enhancer is Located Upstream of an Immediate Early Gene of Human Cytomegalovirus"; Cell, vol. 41, Issue No. 2; 1985; pp. 521-530.

(Continued)

*Primary Examiner* — Sean McGarry
(74) *Attorney, Agent, or Firm* — Cantor Colburn LLP

(57) ABSTRACT

An RNA interference (RNAi) strategy is provided based on use of artificial microRNA (amiR) to reduce NKCC1 expression. In particular, a method is provided that achieves neuron-specific expression of specific amiR against NKCC1 by using a human Synapsin promoter to drive transgene expression.

15 Claims, 5 Drawing Sheets
Specification includes a Sequence Listing.

(56) References Cited

OTHER PUBLICATIONS

Chapleau et al; "Dendritic spine pathologies in hippocampal pyramidal neurons from Rett syndrome brain and after expression of Rett-associated MECP2 mutations"; Neurobiology of Disease, vol. 35, Issue No. 2; 2009; pp. 219-233.
Chiorini et al ; "Cloning of Adeno-Associated Virus Type 4 (AAV4) and Generation Recombinant AAV4 Particles"; Jounral of Virology, vol. 71, Issue No. 9; 1997; pp. 6823-6833.
Chiorini et al; "Cloning and Characterization of Adeno-Associated Virus Type 5"; Journal of Virology, vol. 73, Issue i No. 2; 1999; pp. 1309-1319.
Deidda et al; "Reversing excitatory GABAAR signaling restores synaptic plasticity and memory in a mouse model of Down syndrome"; Nature Medicine, vol. 21, Issue No. 4; 2015; pp. 1-46.
Galka-Marciniak, Paulina et al., "siRNA release from pri-miRNA scaffolds is controlled by the sequence and structure of RNA", Biochimica et Biophysica Acta, vol. 1859; 2016; pp. 639-649.
Gao et al; "Novel adeno-associated viruses from rhesus monkeys as vectors for human gene therapy"; PNAS, vol. 99, issue No. 18; 2002; pp. 11854-11859.
International Search Report for International Publication No. PCT/EP2018/059255; International Filing Date: Apr. 11, 2018; dated Jun. 18, 2018; 6 pages
Jayakumar, Arumugam P. et al., "Na—K—Cl cotransporter-1 in the mechanism of cell swelling in custured astrocytes after fluid percussion injury", Journal of Neurochemistry, vol. 117: 2011; pp. 437-448.
Kwok-Tung, Lu et al.; "NKCC1 mediates traumatic brain injury-induced hippocampal neurogenesis through CREB phosphorylation and HIF-1x expression"; Pflugers Arch—Eur J Physiol, vol. 467: 2015; pp. 1651-1661.
Machado-Salas; "Abnormal dendritic patterns and aberrant spine development in Bourneville's disease—a Golgi survey"; Clinical Neuropathology, vol. 3, Issue No. 2; 1984; pp. 52-58.
Martinez De Lagran et al; "Dyrk1A Influences Neuronal Morphogenesis Through Regulation of Cytoskeletal Dynamics in Mammalian Cortical Neurons"; Cerebral Cortex, vol. 22, Issue No. 12; 2012; pp. 2867-2877.
Mori et al; "Two novel adeno-associated viruses from cynomolgus monkey: pseudotyping characterization of capsid protein"; Virology, vol. 330, Issue No. 2; 2004; pp. 375-383.
Muramatsu et al; "Nucleotide Sequencing and Generation of an Infectious Clone of Adeno-Associated Virus 3"; Journal of Virology, vol. 221, Issue No. 1; 1996; pp. 208-217.
Piccioli et al; "Neuroantibodies: Ectopic Expression of a Recombinant Anti-Substance P Antibody in the Central Nervous System of Transgenic Mice"; Neuron, vol. 15, Issue No. 2; 1995; pp. 373-384.
Piccioli et al; "Neuroantibodies: Molecular cloning of a monocional antibody against substance P for expression in the central nervous system"; PNAS, vol. 88, Issue No. 13; 1991; pp. 5611-5615.
Shade et al; "Nucleotide Sequencing and Genome Organization of Human Parvovirus B19 Isolated from the Serum of a Child During Aplastic Crisis"; Journal of Virology, vol. 58, Issue No. 3; 1986; pp. 921-936.
Srivastava et al; "Nucleotide Sequence and Organization of the Adeno-Assoclateo Virus 2 Genome"; Journal of Virology, vol. 45, Issue No. 2; 1983; pp. 555-564.
Van Den Berg, Fiona T., et al., "Design of Effective Primary MicroRNA Mimics With Different Basal Stem Conformations", Molecular Therapy—Nucleic Acids (2016) 5; pp. 1-12.
Written Opinion of the International Searching Authority for International Application No. PCT/EP2018/059255; International Filing Date: Apr. 11, 2018; dated Jun. 18, 2018; 6 pages.
Xiao et al; "Gene Therapy Vectors Based on Adeno-Associated Virus Type 1"; Journal of Virology, vol. 73, Issue No. 5; 1999; pp. 3994-4003.

artificial miRNAs (amiR) against hNKCC1

SEQUENCE LISTING

<160> NUMBER OF SEQ ID NOS: 92

<210> SEQ ID NO 1
<211> LENGTH: 21
<212> TYPE: DNA
<213> ORGANISM: Artificial Sequence
<220> FEATURE:
<223> OTHER INFORMATION: amiR sequence

<400> SEQUENCE: 1
ttccacactt actaccacat c                                              21

<210> SEQ ID NO 2
<211> LENGTH: 21
<212> TYPE: DNA
<213> ORGANISM: Artificial Sequence
<220> FEATURE:
<223> OTHER INFORMATION: amiR sequence

<400> SEQUENCE: 2
tacatatcca catccctcat a                                              21

<210> SEQ ID NO 3
<211> LENGTH: 21
<212> TYPE: DNA
<213> ORGANISM: Artificial Sequence
<220> FEATURE:
<223> OTHER INFORMATION: amiR sequence

<400> SEQUENCE: 3
tatacatatc cacatccctc a                                              21

<210> SEQ ID NO 4
<211> LENGTH: 21
<212> TYPE: DNA
<213> ORGANISM: Artificial Sequence
<220> FEATURE:
<223> OTHER INFORMATION: amiR sequence

<400> SEQUENCE: 4
tccacactta ctaccacatc c                                              21

<210> SEQ ID NO 5
<211> LENGTH: 21
<212> TYPE: DNA
<213> ORGANISM: Artificial Sequence
<220> FEATURE:
<223> OTHER INFORMATION: amiR sequence

<400> SEQUENCE: 5
tattccacac ttactaccac a                                              21

<210> SEQ ID NO 6
<211> LENGTH: 21
<212> TYPE: DNA
<213> ORGANISM: Artificial Sequence
<220> FEATURE:
<223> OTHER INFORMATION: amiR sequence

<400> SEQUENCE: 6
ttaacctgat ctgccggtat g                                              21

<210> SEQ ID NO 7
<211> LENGTH: 21
<212> TYPE: DNA
<213> ORGANISM: Artificial Sequence
<220> FEATURE:
<223> OTHER INFORMATION: amiR sequence

<400> SEQUENCE: 7
taagcaactc caccacggtt t                                              21

<210> SEQ ID NO 8
<211> LENGTH: 21
<212> TYPE: DNA
<213> ORGANISM: Artificial Sequence
<220> FEATURE:
<223> OTHER INFORMATION: amiR sequence

<400> SEQUENCE: 8
atatccacat ccctcatatc t                                              21

<210> SEQ ID NO 9
<211> LENGTH: 21
<212> TYPE: DNA
<213> ORGANISM: Artificial Sequence
<220> FEATURE:
<223> OTHER INFORMATION: amiR sequence

<400> SEQUENCE: 9
atacatatcc acatccctca t                                              21

<210> SEQ ID NO 10
<211> LENGTH: 21
<212> TYPE: DNA
<213> ORGANISM: Artificial Sequence
<220> FEATURE:
<223> OTHER INFORMATION: amiR sequence

<400> SEQUENCE: 10
attccacact tactaccaca t                                              21

<210> SEQ ID NO 11
<211> LENGTH: 21
<212> TYPE: DNA
<213> ORGANISM: Artificial Sequence
<220> FEATURE:
<223> OTHER INFORMATION: amiR sequence

<400> SEQUENCE: 11
atattccaca cttactacca c                                              21

<210> SEQ ID NO 12
<211> LENGTH: 21
<212> TYPE: DNA
<213> ORGANISM: Artificial Sequence

```
<220> FEATURE:
<223> OTHER INFORMATION: amiR sequence

<400> SEQUENCE: 12
taacctgatc tgccggtatg t                                              21

<210> SEQ ID NO 13
<211> LENGTH: 21
<212> TYPE: DNA
<213> ORGANISM: Artificial Sequence
<220> FEATURE:
<223> OTHER INFORMATION: amiR sequence

<400> SEQUENCE: 13
atttaacctg atctgccggt a                                              21

<210> SEQ ID NO 14
<211> LENGTH: 21
<212> TYPE: DNA
<213> ORGANISM: Artificial Sequence
<220> FEATURE:
<223> OTHER INFORMATION: amiR sequence

<400> SEQUENCE: 14
tgaatagaag gtaaggacac t                                              21

<210> SEQ ID NO 15
<211> LENGTH: 21
<212> TYPE: DNA
<213> ORGANISM: Artificial Sequence
<220> FEATURE:
<223> OTHER INFORMATION: amiR sequence

<400> SEQUENCE: 15
atgaatagaa ggtaaggaca c                                              21

<210> SEQ ID NO 16
<211> LENGTH: 21
<212> TYPE: DNA
<213> ORGANISM: Artificial Sequence
<220> FEATURE:
<223> OTHER INFORMATION: amiR sequence

<400> SEQUENCE: 16
tacaaggact gatagaccta t                                              21

<210> SEQ ID NO 17
<211> LENGTH: 21
<212> TYPE: DNA
<213> ORGANISM: Artificial Sequence
<220> FEATURE:
<223> OTHER INFORMATION: amiR sequence

<400> SEQUENCE: 17
ttacaaggac tgatagacct a                                              21

<210> SEQ ID NO 18
<211> LENGTH: 21
<212> TYPE: DNA
<213> ORGANISM: Artificial Sequence
<220> FEATURE:
<223> OTHER INFORMATION: amiR sequence

<400> SEQUENCE: 18
attacaagga ctgatagacc t                                              21
```

```
<210> SEQ ID NO 19
<211> LENGTH: 21
<212> TYPE: DNA
<213> ORGANISM: Artificial Sequence
<220> FEATURE:
<223> OTHER INFORMATION: amiR sequence

<400> SEQUENCE: 19
ttaagcaact ccaccacggt t                                              21

<210> SEQ ID NO 20
<211> LENGTH: 21
<212> TYPE: DNA
<213> ORGANISM: Artificial Sequence
<220> FEATURE:
<223> OTHER INFORMATION: amiR sequence

<400> SEQUENCE: 20
acgaattgaa tgctgcagtg c                                              21

<210> SEQ ID NO 21
<211> LENGTH: 21
<212> TYPE: DNA
<213> ORGANISM: Artificial Sequence
<220> FEATURE:
<223> OTHER INFORMATION: amiR sequence

<400> SEQUENCE: 21
ctcattatct gttattcgcc a                                              21

<210> SEQ ID NO 22
<211> LENGTH: 21
<212> TYPE: DNA
<213> ORGANISM: Artificial Sequence
<220> FEATURE:
<223> OTHER INFORMATION: amiR sequence

<400> SEQUENCE: 22
aatagaaggt aaggacactc t                                              21

<210> SEQ ID NO 23
<211> LENGTH: 21
<212> TYPE: DNA
<213> ORGANISM: Artificial Sequence
<220> FEATURE:
<223> OTHER INFORMATION: amiR sequence

<400> SEQUENCE: 23
tactaataca cccttgatcc a                                              21

<210> SEQ ID NO 24
<211> LENGTH: 21
<212> TYPE: DNA
<213> ORGANISM: Artificial Sequence
<220> FEATURE:
<223> OTHER INFORMATION: amiR sequence

<400> SEQUENCE: 24
tattgctgaa gtagacaatc c                                              21

<210> SEQ ID NO 25
<211> LENGTH: 21
<212> TYPE: DNA
<213> ORGANISM: Artificial Sequence
<220> FEATURE:
<223> OTHER INFORMATION: amiR sequence
```

```
<400> SEQUENCE: 25
aatccaacca catacatagc a                                              21

<210> SEQ ID NO 26
<211> LENGTH: 21
<212> TYPE: DNA
<213> ORGANISM: Artificial Sequence
<220> FEATURE:
<223> OTHER INFORMATION: amiR sequence

<400> SEQUENCE: 26
ttccttaagc aactccacca c                                              21

<210> SEQ ID NO 27
<211> LENGTH: 21
<212> TYPE: DNA
<213> ORGANISM: Artificial Sequence
<220> FEATURE:
<223> OTHER INFORMATION: amiR sequence

<400> SEQUENCE: 27
aattgaatgc tgcagtgcat t                                              21

<210> SEQ ID NO 28
<211> LENGTH: 21
<212> TYPE: DNA
<213> ORGANISM: Artificial Sequence
<220> FEATURE:
<223> OTHER INFORMATION: amiR sequence

<400> SEQUENCE: 28
atccacatcc ctcatatctg c                                              21

<210> SEQ ID NO 29
<211> LENGTH: 21
<212> TYPE: DNA
<213> ORGANISM: Artificial Sequence
<220> FEATURE:
<223> OTHER INFORMATION: amiR sequence

<400> SEQUENCE: 29
tatccacatc cctcatatct g                                              21

<210> SEQ ID NO 30
<211> LENGTH: 21
<212> TYPE: DNA
<213> ORGANISM: Artificial Sequence
<220> FEATURE:
<223> OTHER INFORMATION: amiR sequence

<400> SEQUENCE: 30
cacacttact accacatcct t                                              21

<210> SEQ ID NO 31
<211> LENGTH: 21
<212> TYPE: DNA
<213> ORGANISM: Artificial Sequence
<220> FEATURE:
<223> OTHER INFORMATION: amiR sequence

<400> SEQUENCE: 31
ttcaacagtg gttgagttgc a                                              21

<210> SEQ ID NO 32
```

```
<211> LENGTH: 21
<212> TYPE: DNA
<213> ORGANISM: Artificial Sequence
<220> FEATURE:
<223> OTHER INFORMATION: amiR sequence

<400> SEQUENCE: 32
agcaaagtag ccatcgctct c                                              21

<210> SEQ ID NO 33
<211> LENGTH: 21
<212> TYPE: DNA
<213> ORGANISM: Artificial Sequence
<220> FEATURE:
<223> OTHER INFORMATION: amiR sequence

<400> SEQUENCE: 33
aagcaaagta gccatcgctc t                                              21

<210> SEQ ID NO 34
<211> LENGTH: 21
<212> TYPE: DNA
<213> ORGANISM: Artificial Sequence
<220> FEATURE:
<223> OTHER INFORMATION: amiR sequence

<400> SEQUENCE: 34
taagcaaagt agccatcgct c                                              21

<210> SEQ ID NO 35
<211> LENGTH: 21
<212> TYPE: DNA
<213> ORGANISM: Artificial Sequence
<220> FEATURE:
<223> OTHER INFORMATION: amiR sequence

<400> SEQUENCE: 35
acttgctaag caaagtagcc a                                              21

<210> SEQ ID NO 36
<211> LENGTH: 21
<212> TYPE: DNA
<213> ORGANISM: Artificial Sequence
<220> FEATURE:
<223> OTHER INFORMATION: amiR sequence

<400> SEQUENCE: 36
aacttgctaa gcaaagtagc c                                              21

<210> SEQ ID NO 37
<211> LENGTH: 21
<212> TYPE: DNA
<213> ORGANISM: Artificial Sequence
<220> FEATURE:
<223> OTHER INFORMATION: amiR sequence

<400> SEQUENCE: 37
aacctgatct gccggtatgt c                                              21

<210> SEQ ID NO 38
<211> LENGTH: 21
<212> TYPE: DNA
<213> ORGANISM: Artificial Sequence
<220> FEATURE:
<223> OTHER INFORMATION: amiR sequence

<400> SEQUENCE: 38
```

```
ttctgcagta tacgtgacca c                                              21

<210> SEQ ID NO 39
<211> LENGTH: 21
<212> TYPE: DNA
<213> ORGANISM: Artificial Sequence
<220> FEATURE:
<223> OTHER INFORMATION: amiR sequence

<400> SEQUENCE: 39
acaacgtact aatacaccct t                                              21

<210> SEQ ID NO 40
<211> LENGTH: 21
<212> TYPE: DNA
<213> ORGANISM: Artificial Sequence
<220> FEATURE:
<223> OTHER INFORMATION: amiR sequence

<400> SEQUENCE: 40
catacaacgt actaatacac c                                              21

<210> SEQ ID NO 41
<211> LENGTH: 21
<212> TYPE: DNA
<213> ORGANISM: Artificial Sequence
<220> FEATURE:
<223> OTHER INFORMATION: amiR sequence

<400> SEQUENCE: 41
tgttccttaa gcaactccac c                                              21

<210> SEQ ID NO 42
<211> LENGTH: 21
<212> TYPE: DNA
<213> ORGANISM: Artificial Sequence
<220> FEATURE:
<223> OTHER INFORMATION: amiR sequence

<400> SEQUENCE: 42
aggagtgttc ctttgggtat g                                              21

<210> SEQ ID NO 43
<211> LENGTH: 21
<212> TYPE: DNA
<213> ORGANISM: Artificial Sequence
<220> FEATURE:
<223> OTHER INFORMATION: amiR sequence

<400> SEQUENCE: 43
taggagtgtt cctttgggta t                                              21

<210> SEQ ID NO 44
<211> LENGTH: 21
<212> TYPE: DNA
<213> ORGANISM: Artificial Sequence
<220> FEATURE:
<223> OTHER INFORMATION: amiR sequence

<400> SEQUENCE: 44
ctaggagtgt tcctttgggt a                                              21

<210> SEQ ID NO 45
<211> LENGTH: 21
<212> TYPE: DNA
```

```
<213> ORGANISM: Artificial Sequence
<220> FEATURE:
<223> OTHER INFORMATION: amiR sequence

<400> SEQUENCE: 45
agaacctaca gatactgcaa t                                              21

<210> SEQ ID NO 46
<211> LENGTH: 21
<212> TYPE: DNA
<213> ORGANISM: Artificial Sequence
<220> FEATURE:
<223> OTHER INFORMATION: amiR sequence

<400> SEQUENCE: 46
tcattaacgt ttccagtggc a                                              21

<210> SEQ ID NO 47
<211> LENGTH: 21
<212> TYPE: DNA
<213> ORGANISM: Artificial Sequence
<220> FEATURE:
<223> OTHER INFORMATION: amiR sequence

<400> SEQUENCE: 47
tgtcattaac gtttccagtg g                                              21

<210> SEQ ID NO 48
<211> LENGTH: 21
<212> TYPE: DNA
<213> ORGANISM: Artificial Sequence
<220> FEATURE:
<223> OTHER INFORMATION: amiR sequence

<400> SEQUENCE: 48
aatcctgaca ccatactcat t                                              21

<210> SEQ ID NO 49
<211> LENGTH: 21
<212> TYPE: DNA
<213> ORGANISM: Artificial Sequence
<220> FEATURE:
<223> OTHER INFORMATION: amiR sequence

<400> SEQUENCE: 49
aaatcctgac accatactca t                                              21

<210> SEQ ID NO 50
<211> LENGTH: 21
<212> TYPE: DNA
<213> ORGANISM: Artificial Sequence
<220> FEATURE:
<223> OTHER INFORMATION: amiR sequence

<400> SEQUENCE: 50
tcactaggga tgctaatgct g                                              21

<210> SEQ ID NO 51
<211> LENGTH: 21
<212> TYPE: DNA
<213> ORGANISM: Artificial Sequence
<220> FEATURE:
<223> OTHER INFORMATION: amiR sequence

<400> SEQUENCE: 51
tacagcccaa ggactatcac a                                              21
```

```
<210> SEQ ID NO 52
<211> LENGTH: 21
<212> TYPE: DNA
<213> ORGANISM: Artificial Sequence
<220> FEATURE:
<223> OTHER INFORMATION: amiR sequence

<400> SEQUENCE: 52
tatacagccc aaggactatc a                                              21

<210> SEQ ID NO 53
<211> LENGTH: 21
<212> TYPE: DNA
<213> ORGANISM: Artificial Sequence
<220> FEATURE:
<223> OTHER INFORMATION: amiR sequence

<400> SEQUENCE: 53
aagacgaatt gaatgctgca g                                              21

<210> SEQ ID NO 54
<211> LENGTH: 21
<212> TYPE: DNA
<213> ORGANISM: Artificial Sequence
<220> FEATURE:
<223> OTHER INFORMATION: amiR sequence

<400> SEQUENCE: 54
aagacgaatt gaatgctgca g                                              21

<210> SEQ ID NO 55
<211> LENGTH: 21
<212> TYPE: DNA
<213> ORGANISM: Artificial Sequence
<220> FEATURE:
<223> OTHER INFORMATION: amiR sequence

<400> SEQUENCE: 55
tttcatggct tgtcttcgag g                                              21

<210> SEQ ID NO 56
<211> LENGTH: 21
<212> TYPE: DNA
<213> ORGANISM: Artificial Sequence
<220> FEATURE:
<223> OTHER INFORMATION: amiR sequence

<400> SEQUENCE: 56
atctgcttgc aaccaatctt t                                              21

<210> SEQ ID NO 57
<211> LENGTH: 21
<212> TYPE: DNA
<213> ORGANISM: Artificial Sequence
<220> FEATURE:
<223> OTHER INFORMATION: amiR sequence

<400> SEQUENCE: 57
atatctgctt gcaaccaatc t                                              21

<210> SEQ ID NO 58
<211> LENGTH: 21
<212> TYPE: DNA
<213> ORGANISM: Artificial Sequence
<220> FEATURE:
```

<223> OTHER INFORMATION: amiR sequence

<400> SEQUENCE: 58
catatctgct tgcaaccaat c                                             21

<210> SEQ ID NO 59
<211> LENGTH: 21
<212> TYPE: DNA
<213> ORGANISM: Artificial Sequence
<220> FEATURE:
<223> OTHER INFORMATION: amiR sequence

<400> SEQUENCE: 59
aacagtggtt gagttgcagt c                                             21

<210> SEQ ID NO 60
<211> LENGTH: 21
<212> TYPE: DNA
<213> ORGANISM: Artificial Sequence
<220> FEATURE:
<223> OTHER INFORMATION: amiR sequence

<400> SEQUENCE: 60
ttgctaagca aagtagccat c                                             21

<210> SEQ ID NO 61
<211> LENGTH: 21
<212> TYPE: DNA
<213> ORGANISM: Artificial Sequence
<220> FEATURE:
<223> OTHER INFORMATION: amiR sequence

<400> SEQUENCE: 61
attatctgtt attcgccatg g                                             21

<210> SEQ ID NO 62
<211> LENGTH: 21
<212> TYPE: DNA
<213> ORGANISM: Artificial Sequence
<220> FEATURE:
<223> OTHER INFORMATION: amiR sequence

<400> SEQUENCE: 62
agctcattat ctgttattcg c                                             21

<210> SEQ ID NO 63
<211> LENGTH: 21
<212> TYPE: DNA
<213> ORGANISM: Artificial Sequence
<220> FEATURE:
<223> OTHER INFORMATION: amiR sequence

<400> SEQUENCE: 63
tgggtatcat aatagtagtg c                                             21

<210> SEQ ID NO 64
<211> LENGTH: 21
<212> TYPE: DNA
<213> ORGANISM: Artificial Sequence
<220> FEATURE:
<223> OTHER INFORMATION: amiR sequence

<400> SEQUENCE: 64
gtgggtatca taatagtagt g                                             21

```
<210> SEQ ID NO 65
<211> LENGTH: 21
<212> TYPE: DNA
<213> ORGANISM: Artificial Sequence
<220> FEATURE:
<223> OTHER INFORMATION: amiR sequence

<400> SEQUENCE: 65
acctattcca gcttgaccca c                                              21

<210> SEQ ID NO 66
<211> LENGTH: 21
<212> TYPE: DNA
<213> ORGANISM: Artificial Sequence
<220> FEATURE:
<223> OTHER INFORMATION: amiR sequence

<400> SEQUENCE: 66
caaaggcgaa gattagacca a                                              21

<210> SEQ ID NO 67
<211> LENGTH: 21
<212> TYPE: DNA
<213> ORGANISM: Artificial Sequence
<220> FEATURE:
<223> OTHER INFORMATION: amiR sequence

<400> SEQUENCE: 67
aaagaatcac gactgtaatg g                                              21

<210> SEQ ID NO 68
<211> LENGTH: 21
<212> TYPE: DNA
<213> ORGANISM: Artificial Sequence
<220> FEATURE:
<223> OTHER INFORMATION: amiR sequence

<400> SEQUENCE: 68
aacacaagaa cctacagata c                                              21

<210> SEQ ID NO 69
<211> LENGTH: 21
<212> TYPE: DNA
<213> ORGANISM: Artificial Sequence
<220> FEATURE:
<223> OTHER INFORMATION: amiR sequence

<400> SEQUENCE: 69
agtacagttt gttagctctg t                                              21

<210> SEQ ID NO 70
<211> LENGTH: 21
<212> TYPE: DNA
<213> ORGANISM: Artificial Sequence
<220> FEATURE:
<223> OTHER INFORMATION: amiR sequence

<400> SEQUENCE: 70
ttaatttgca ggctgcagaa g                                              21

<210> SEQ ID NO 71
<211> LENGTH: 21
<212> TYPE: DNA
<213> ORGANISM: Artificial Sequence
<220> FEATURE:
<223> OTHER INFORMATION: amiR sequence
```

```
<400> SEQUENCE: 71
ttgggagcac tcactaggga t                                               21

<210> SEQ ID NO 72
<211> LENGTH: 21
<212> TYPE: DNA
<213> ORGANISM: Artificial Sequence
<220> FEATURE:
<223> OTHER INFORMATION: amiR sequence

<400> SEQUENCE: 72
tttgggagca ctcactaggg a                                               21

<210> SEQ ID NO 73
<211> LENGTH: 21
<212> TYPE: DNA
<213> ORGANISM: Artificial Sequence
<220> FEATURE:
<223> OTHER INFORMATION: amiR sequence

<400> SEQUENCE: 73
aatgcatatg atgcaaggaa g                                               21

<210> SEQ ID NO 74
<211> LENGTH: 21
<212> TYPE: DNA
<213> ORGANISM: Artificial Sequence
<220> FEATURE:
<223> OTHER INFORMATION: amiR sequence

<400> SEQUENCE: 74
ctgcagtgca ttcaggtaag t                                               21

<210> SEQ ID NO 75
<211> LENGTH: 21
<212> TYPE: DNA
<213> ORGANISM: Artificial Sequence
<220> FEATURE:
<223> OTHER INFORMATION: amiR sequence

<400> SEQUENCE: 75
tgctgcagtg cattcaggta a                                               21

<210> SEQ ID NO 76
<211> LENGTH: 21
<212> TYPE: DNA
<213> ORGANISM: Artificial Sequence
<220> FEATURE:
<223> OTHER INFORMATION: amiR sequence

<400> SEQUENCE: 76
ttgaatgctg cagtgcattc a                                               21

<210> SEQ ID NO 77
<211> LENGTH: 21
<212> TYPE: DNA
<213> ORGANISM: Artificial Sequence
<220> FEATURE:
<223> OTHER INFORMATION: amiR sequence

<400> SEQUENCE: 77
tctctttcat ggcttgtctt c                                               21

<210> SEQ ID NO 78
<211> LENGTH: 21
```

```
<212> TYPE: DNA
<213> ORGANISM: Artificial Sequence
<220> FEATURE:
<223> OTHER INFORMATION: amiR sequence

<400> SEQUENCE: 78
ttggcttgat cgatggacat c                                              21

<210> SEQ ID NO 79
<211> LENGTH: 21
<212> TYPE: DNA
<213> ORGANISM: Artificial Sequence
<220> FEATURE:
<223> OTHER INFORMATION: amiR sequence

<400> SEQUENCE: 79
ttgagttgca gtcttgccat c                                              21

<210> SEQ ID NO 80
<211> LENGTH: 21
<212> TYPE: DNA
<213> ORGANISM: Artificial Sequence
<220> FEATURE:
<223> OTHER INFORMATION: amiR sequence

<400> SEQUENCE: 80
tttcaacagt ggttgagttg c                                              21

<210> SEQ ID NO 81
<211> LENGTH: 21
<212> TYPE: DNA
<213> ORGANISM: Artificial Sequence
<220> FEATURE:
<223> OTHER INFORMATION: amiR sequence

<400> SEQUENCE: 81
gaacttgcta agcaaagtag c                                              21

<210> SEQ ID NO 82
<211> LENGTH: 21
<212> TYPE: DNA
<213> ORGANISM: Artificial Sequence
<220> FEATURE:
<223> OTHER INFORMATION: amiR sequence

<400> SEQUENCE: 82
aagtctatcc ggaacttgct a                                              21

<210> SEQ ID NO 83
<211> LENGTH: 21
<212> TYPE: DNA
<213> ORGANISM: Artificial Sequence
<220> FEATURE:
<223> OTHER INFORMATION: amiR sequence

<400> SEQUENCE: 83
aactcattta acctgatctg c                                              21

<210> SEQ ID NO 84
<211> LENGTH: 21
<212> TYPE: DNA
<213> ORGANISM: Artificial Sequence
<220> FEATURE:
<223> OTHER INFORMATION: amiR sequence

<400> SEQUENCE: 84
```
taaccatgcc atgtagagag c                                              21

<210> SEQ ID NO 85
<211> LENGTH: 21
<212> TYPE: DNA
<213> ORGANISM: Artificial Sequence
<220> FEATURE:
<223> OTHER INFORMATION: amiR sequence

<400> SEQUENCE: 85
ttctaaccat gccatgtaga g                                              21

<210> SEQ ID NO 86
<211> LENGTH: 21
<212> TYPE: DNA
<213> ORGANISM: Artificial Sequence
<220> FEATURE:
<223> OTHER INFORMATION: amiR sequence

<400> SEQUENCE: 86
ctttgggtat ggctgactga g                                              21

<210> SEQ ID NO 87
<211> LENGTH: 21
<212> TYPE: DNA
<213> ORGANISM: Artificial Sequence
<220> FEATURE:
<223> OTHER INFORMATION: amiR sequence

<400> SEQUENCE: 87
ttcctttggg tatggctgac t                                              21

<210> SEQ ID NO 88
<211> LENGTH: 21
<212> TYPE: DNA
<213> ORGANISM: Artificial Sequence
<220> FEATURE:
<223> OTHER INFORMATION: amiR sequence

<400> SEQUENCE: 88
atacatagca actgcaacag c                                              21

<210> SEQ ID NO 89
<211> LENGTH: 21
<212> TYPE: DNA
<213> ORGANISM: Artificial Sequence
<220> FEATURE:
<223> OTHER INFORMATION: amiR sequence

<400> SEQUENCE: 89
agatgttgtc cttacataga g                                              21

<210> SEQ ID NO 90
<211> LENGTH: 26
<212> TYPE: DNA
<213> ORGANISM: Artificial Sequence
<220> FEATURE:
<223> OTHER INFORMATION: 5'flanking region

<400> SEQUENCE: 90
tggaggcttg ctgaaggctg tatgct                                         26

<210> SEQ ID NO 91
<211> LENGTH: 19
<212> TYPE: DNA
<213> ORGANISM: Artificial Sequence

```
<220> FEATURE:
<223> OTHER INFORMATION: loop forming sequence

<400> SEQUENCE: 91
gttttggcca ctgactgac                                                    19

<210> SEQ ID NO 92
<211> LENGTH: 46
<212> TYPE: DNA
<213> ORGANISM: Artificial Sequence
<220> FEATURE:
<223> OTHER INFORMATION: 3' flanking region

<400> SEQUENCE: 92
caggacacaa ggcctgttac tagcactcac atggaacaaa tggccc                      46
```

METHOD FOR REDUCING THE EXPRESSION OF NKCC1 IN A SUBJECT

CROSS-REFERENCE TO RELATED APPLICATIONS

This application is a U.S. National Phase filing of PCT International Patent Application No. PCT/EP2018/059255, having an international filing date of Apr. 11, 2018, which claims priority to European Patent Application No. 17305434.7, filed Apr. 11, 2017 each of which is hereby incorporated by reference in its entirety.

SEQUENCE LISTING

The Instant Application contains a Sequence Listing which has been submitted electronically in ASCII format and is hereby incorporated by reference in its entirety. Said ASCII copy, created on Oct. 11, 2019 is named "@E0122870.USA (JNP0173US) JNP0173US_ST25 Sequence Listing TXT filed 11 Oct. 2019" and is 17,824 bytes in size.

FIELD OF THE INVENTION

The present invention relates to a vector, a pharmaceutical composition and a method for reducing the expression of NKCC1 in a subject in need thereof.

BACKGROUND OF THE INVENTION

The $Na^+$, $K^+$, $2Cl^-$ cotransporter (NKCC) encoded by SLC12A2 (NKCC1) belongs to the subfamily of cation-chloride cotransporters (CCCs) that provide electroneutral transport of sodium, potassium and chloride across the plasma membrane. Several pieces of evidence show that NKCC1 is involved in the pathogenesis of several diseases via regulation of intracellular chloride concentration. For instance, recent studies show that the chloride cotransporter NKCC1 is overexpressed in the brains of DS mouse models and patients with Down Syndrome (Deidda et al., 2015; WO2015091857A1). Down syndrome (DS) is the most frequent cause of intellectual disability in children and adults. Down syndrome is a genetic disorder caused by the presence of all or part of a third copy of human chromosome 21, therefore is also referred as trisomy 21. Down syndrome is almost invariably characterized by cognitive impairment, memory deficits and learning difficulties. Accordingly, pharmacological treatment with the NKCC1 inhibitor (but also diuretic FDA-approved drug) Bumetanide restores synaptic plasticity and cognitive impairment in the Ts65Dn mouse model of DS (Deidda et al., 2015; WO2015091857A1). However, several data indicated that a life-long treatment with Bumetanide would be required, thus potentially inducing undesirable excessive diuresis (which, would jeopardize treatment compliance) and related side effects of chronic imbalance in a number of electrolytes. Moreover, systemic treatment with Bumetanide would block NKCC1 activity also in organs other than the brain, which may cause ototoxicity (Ben-Ari et al., 2016). So, there is a need to overcome these limitations in the perspective of a therapy for DS based on a reduction of NKCC1 activity.

SUMMARY OF THE INVENTION

The present invention relates to a vector, a pharmaceutical composition and a method for reducing the expression of NKCC1 in a subject in need thereof. The scope of the present invention is defined by the appended claims.

The present invention will be further illustrated by the following figures and examples. which should not be interpreted in any way as limiting the scope of the present invention.

DETAILED DESCRIPTION OF THE INVENTION

Figure 1:
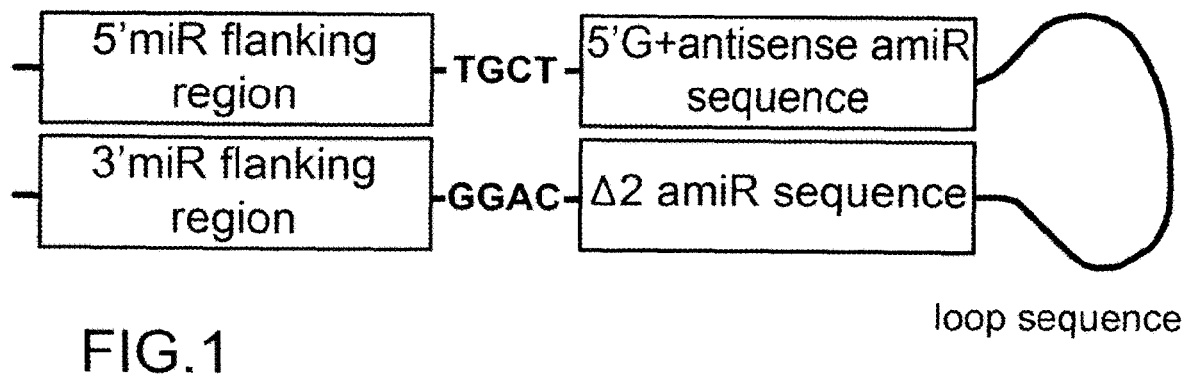
FIG. 1 represents a amiR construct consisting of 5' flanking region derived from a natural miRNA, a TGCT nucleotide overhang, a 5'G+short 21 nucleotide antisense sequence derived from the hNKCC1, a loop forming sequence, a short 19 nucleotides sense sequence derived from hNKCC1 with 2 nucleotides removed (42) to create an internal loop, a CAGG overhang and a 3' flanking region derived from a natural miRNA.
Figure 2:
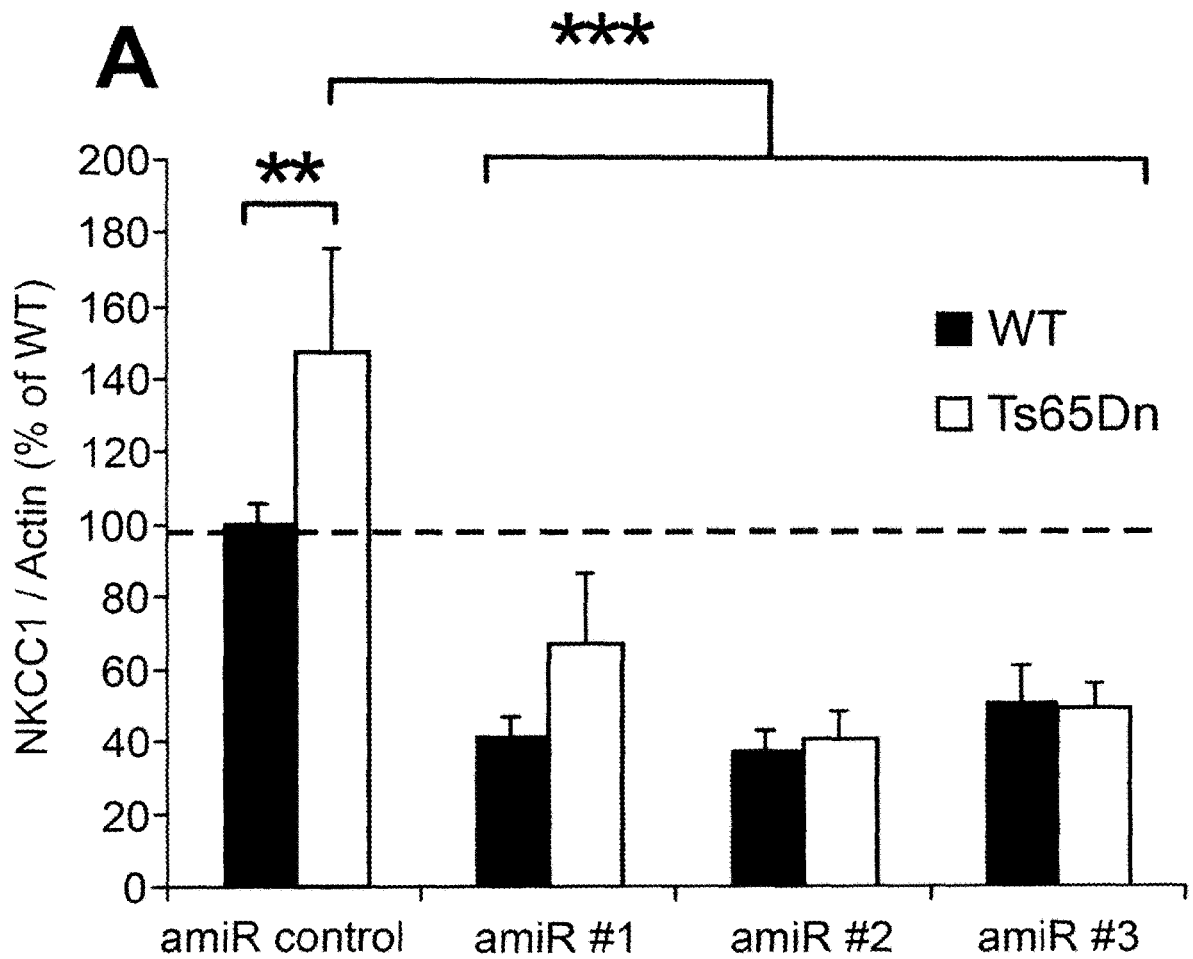
FIG. 2 represents the effect of viral expression of 3 different amiR molecules against mouse NKCC1 on the corresponding level of NKCC1 protein in WT and Ts65Dn neurons in culture. The higher expression of mouse NKCC1 was expressed as percentage of WT cells with control amiR (dashed line) in Ts65Dn neurons in comparison to WT. Viral expression of 3 different amiR molecules reduced mouse NKCC1 protein in both WT and Ts65Dn neurons. Histograms represent average ±SEM. $p<0.01$, *$p<0.001$, post hoc Tukey test following Two-Way ANOVA.
Figure 3:
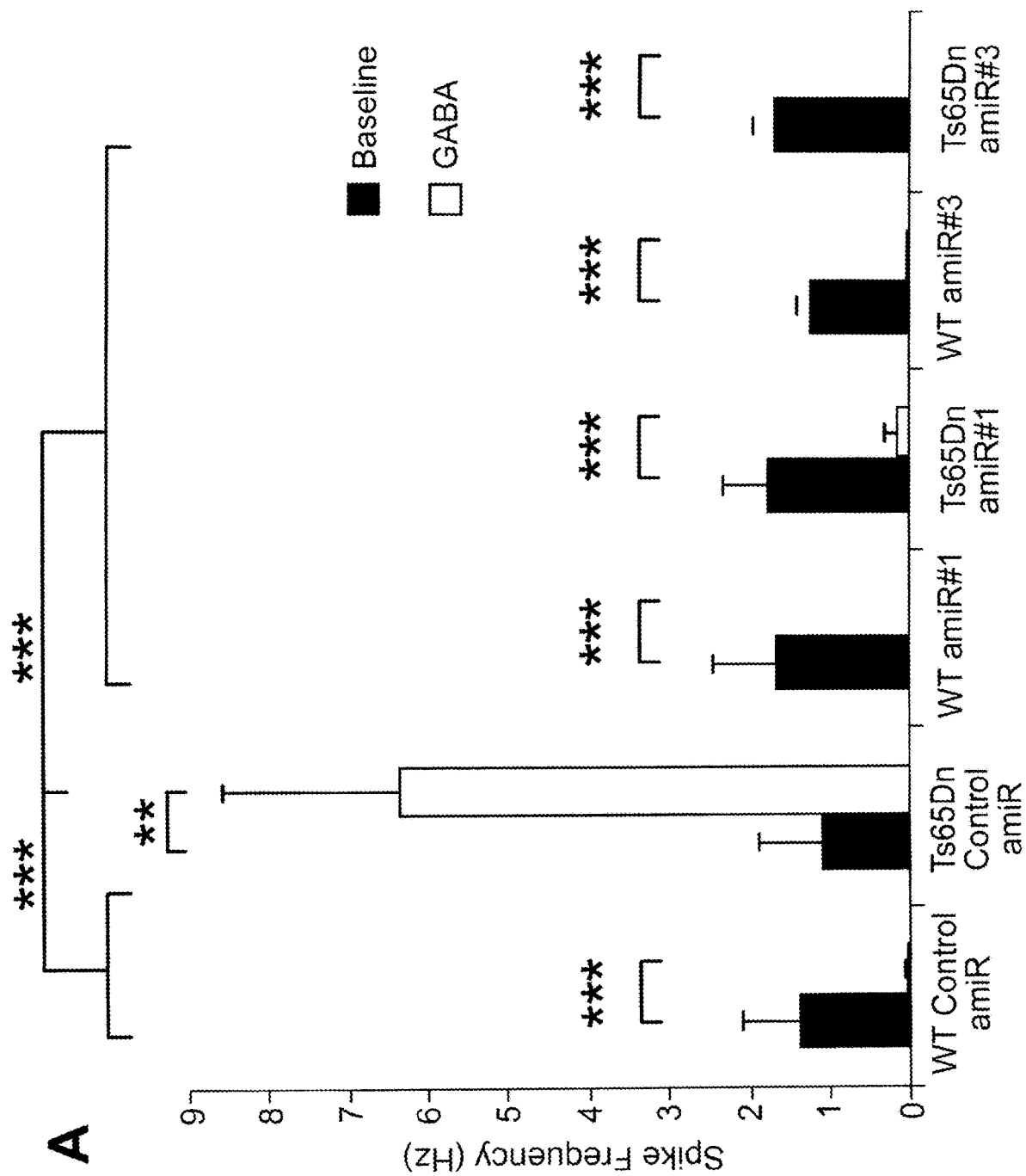
FIG. 3 represents hippocampal neurons in culture from Ts65Dn mice that exhibit excitatory responses to GABA. Spike frequency was decreased in WT neurons with control amiR by bath application of GABA, while it was increased in Ts65Dn neurons. Administration of two different amiR molecules (i.e. amiR #1 and amiR #3 of FIG. 2) by viral delivery reverted excitatory action of GABA in Ts65Dn neurons by reducing spike frequency. Histograms represent average ±SEM. "$p<0.01$, ***$p<0.001$, post hoc Tukey test following Two-Way Repeated-Measure ANOVA.
Figure 4:
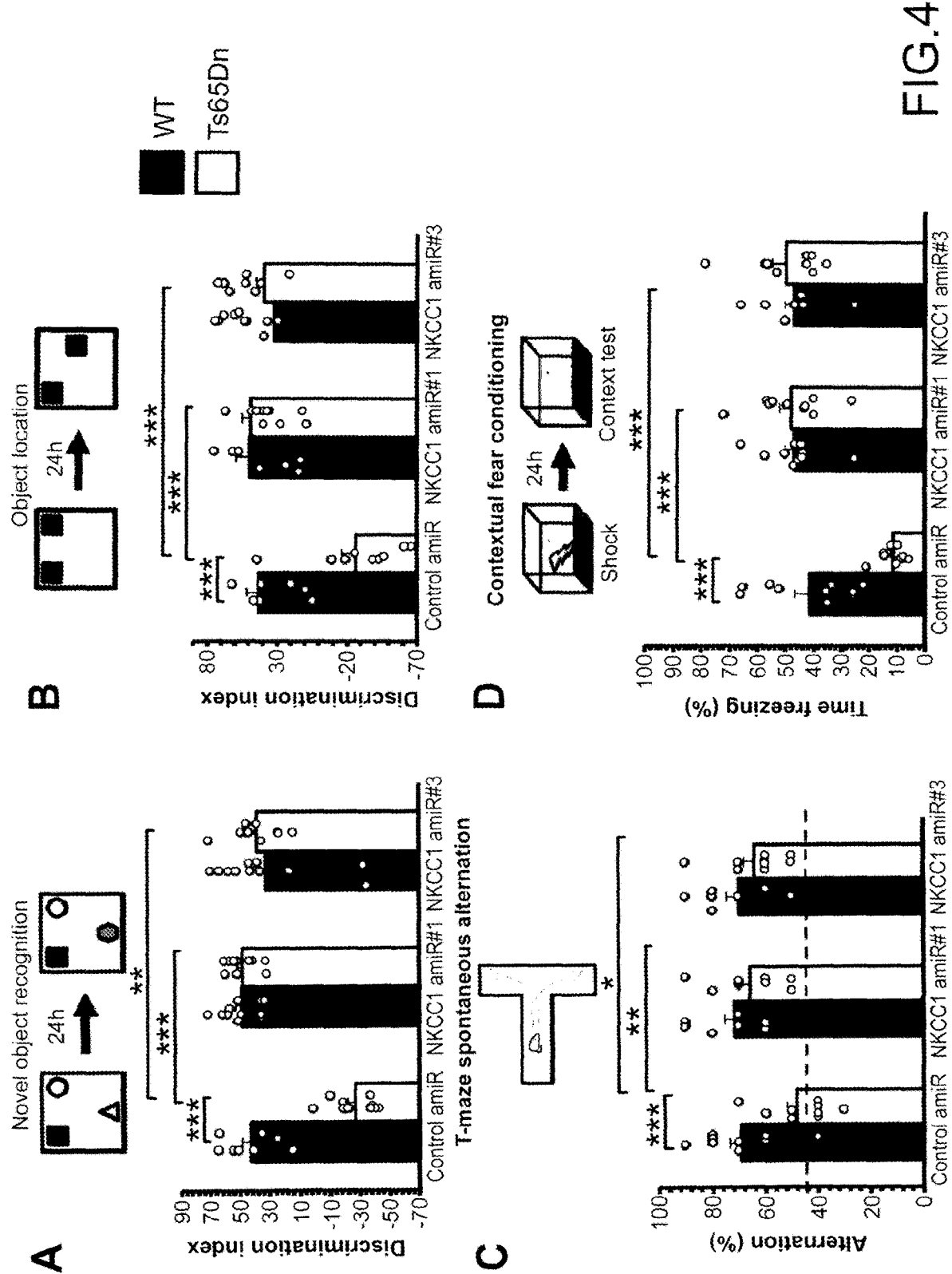
FIG. 4 represents the effect of hippocampal viral delivery of amiR against mouse NKCC1 on cognitive functions in behavioral tasks in Ts65Dn mice. (A) Top, schematic representation of the novel object recognition task. Bottom, Ts65Dn mice showed poor novelty discrimination compared to WT. Viral delivery of two different amiR molecules (i.e. amiR #1 and amiR #3 of FIG. 2) restored object novelty discrimination in Ts65Dn mice. (B) Top, schematic representation of object location test. Bottom, Ts65Dn mice showed strong spatial memory impairment, as compared to WT. Viral delivery of two different amiR molecules restored spatial memory in Ts65Dn mice. (C) Top, schematic representation of T-maze spontaneous alternation test. Bottom, Ts65Dn mice showed reduced alternation compared to WT. Viral delivery of two different amiR molecules restored alternation behavior in Ts65Dn mice. (D) Top, schematic representation of the contextual fear conditioning test. Bottom, Ts65Dn mice showed impaired associative memory in comparison to WT. Viral delivery of two different amiR molecules restored contextual learning in Ts65Dn mice. For all panels, histograms represent average ±SEM, whereas circles indicate data from single animals. For all panels: *$p<0.05$, $p<0.01$, *$p<0.001$, post hoc Tukey test following Two-Way ANOVA.
Figure 5:
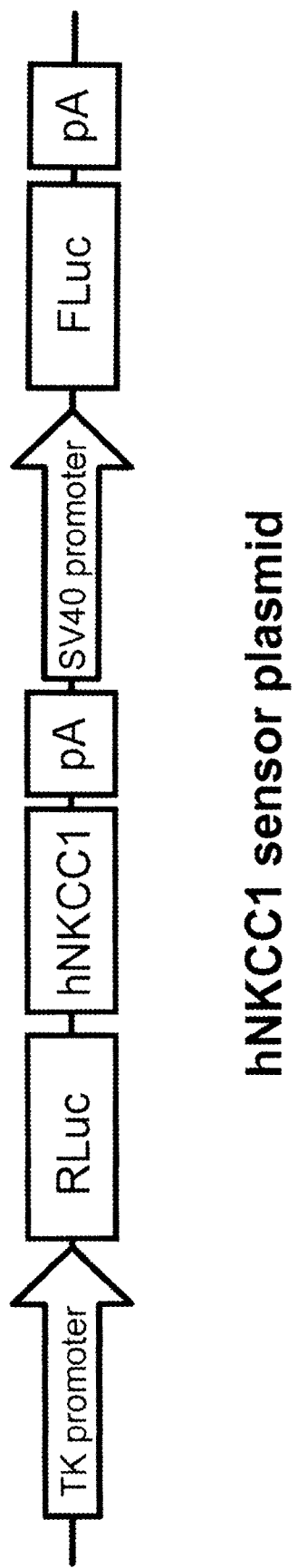
FIG. 5 represents the dual-luciferase sensor plasmids used for screening different amiR molecules against human NKCC1 (hNKCC1) DNA sequence (NM_001046.2). The sensor plasmid expresses Firefly luciferase (FLuc) and Renilla luciferase (RLuc) from two distinct promoters. The hNKCC1 DNA sequence is cloned downstream of RLuc and before the poly-adenylating (pA) signal. When the plasmid is co-transfected in human H293 kidney cells together with the different amiR molecules against hNKCC1, a decrease in the Rluc/Fluc ratio will reflect the silencing activity of the amiR corresponding sequence.

The inventors have developed an RNA interference (RNAi) strategy based on the use of artificial microRNA (amiR) to reduce NKCC1 expression. Artificial microRNA are constructed by replacing the 21-22 nucleotide antisense targeting sequence (the so-called guide strand) of a naturally-occurring primary-microRNA (pri-miRNA) scaffold (for example mouse microRNA 155; Gene Bank accession number: NR_029565.1) with an antisense targeting sequence against hNKCC1. In particular, the inventors have engineered a system to achieve neuron-specific expression of specific amiR against NKCC1 by using a human Synapsin promoter to drive transgene expression.

Accordingly, in a first aspect, the present invention relates to a vector for use in a method of treatment for reducing the expression of NKCC1 in a subject in need thereof, the vector comprising a polynucleotide encoding an amiR capable of reducing the expression of NKCC1, wherein the amiR comprises at least one nucleic acid sequence selected from the group consisting of SEQ ID NOs:4, 8, 15, 16, 18, 23, 25, 39, 40, 44, 45, 53, 57, 64, 66, 67, 68, 69, 82 and 88.

A second aspect of the present invention relates to a pharmaceutical composition for use in a method of treatment for reducing the expression of NKCC1 in a subject in need thereof, the composition comprising a vector according to the invention.

A third aspect of the present invention relates to a method of reducing the expression of NKCC1 in a subject in need thereof, comprising delivering to the subject a therapeutically effective amount of the vector according to the invention.

Further features and advantages of the invention will become apparent from the following detailed description.

As used herein, NKCC for "Na—K—Cl co-transporter" denotes a protein that assists in the active transport of sodium, potassium, and chloride into and out of cells. There are several varieties, or isoforms, of this membrane transport protein, notably NKCC1 and NKCC2. NKCC1 is encoded by SLC12A2 gene (Gene ID 6558) and is widely distributed throughout the body but also in the brain and in particular in the developing animal and human brain. It acts to augment intracellular chloride in neurons and thereby to render GABA more excitatory. Extensive investigations indicate that blocking NKCC1 reduce intracellular chloride thereby augmenting the inhibitory actions of GABA. Exemplary human nucleic and amino acid sequences are represented by the NCBI references sequences NM_001046.2 and NP 001037.1 respectively.

As used herein, the term "subject" refers to both human and animal subjects. Animals include but are not limited to mammals, rodents, primates, monkeys (e.g., macaque, rhesus macaque, or pig tail macaque), canine, feline, bovine, porcine, avian (e.g., chicken), mice, rabbits, and rats. In some embodiments, the subject is typically intended for a human.

In some embodiments, the subject suffers from a disease selected from the group consisting of Down syndrome, Fragile X syndrome, Rett syndrome, Tuberous sclerosis, traumatic brain injury, epilepsy, autism, Schizophrenia, Parkinson's disease, hypertension. Accordingly, the vector of the present invention is particularly suitable for the treatment of the above mentioned disease.

As used herein, the term "Rett syndrome" has its general meaning in the art and refers to an X chromosome-linked neurodevelopmental disorder that leads to developmental reversals, especially in the areas of expressive language and hand use. The clinical features include small hands and feet and a deceleration of the rate of head growth, including microcephaly in some cases. Rett syndrome is associated with neuropathology of dendritic spines, in particular reduced dendritic spine density in hippocampal pyramidal neurons has been found in patients with Rett syndrome (Chapleau C A et al, Neurobiol Dis 2009, 35(2): 219-33).

As used herein, the term "tuberous sclerosis" or "Bourneville's disease" has its general meaning in the art and refers to a neurocutaneous syndrome caused by mutations in one of either of two genes, TSC1 and TSC2, which encode proteins hamartin and tuberin respectively, both of which act as tumor suppressors. Tuberous sclerosis leads to the growth of non-malignant tumors in the brain and other vital organs such as kidneys, heart, eyes, lungs and skin. Different types of dendritic abnormalities have been described in tuberous sclerosis patients (Machado-Salas J P, Clin Neuropathol 1984, 3(2): 52-8).

As used herein, the term "traumatic brain injury" or "TBI" has its general meaning in the art and refers to any microscopic or macroscopic injury, wound, or damage caused by any type of trauma to the head, such as impact to the head or shaking. Traumatic brain injury may be an acquired injury to the brain caused by an external physical force. Common causes of traumatic brain injury include, but are not limited to falls (e.g., falling out of bed, slipping in the bath, falling down steps, falling from ladders and related falls), vehicle-related collisions (e.g., collisions involving cars, motorcycles or bicycles, and pedestrians involved in such accidents), violence (e.g., gunshot wounds, domestic violence, or child abuse (e.g., shaken baby syndrome), sports injuries (e.g., occurring in soccer, boxing, football, baseball, lacrosse, skateboarding, hockey, and other high-impact or extreme sports), explosive blasts and other combat injuries (e.g., from penetrating wounds, severe blows to the head with shrapnel or debris, and falls or bodily collisions with objects following a blast), and the like. Methods for diagnosing TBI are well-established in the art. Traumatic brain injury may also include brain trauma resulting from ischemic events (e.g., stroke), surgery, radiation, or other medical procedures.

As used herein, the term "epilepsy" has its general meaning in the art and refers to a chronic neurological disorder characterized by recurrent unprovoked seizures. These seizures are transient signs and/or symptoms of abnormal, excessive or synchronous neuronal activity in the brain. There are over 40 different types of epilepsy, including without limitation childhood absence epilepsy, juvenile absence epilepsy, benign Rolandic epilepsy, clonic seizures, complex partial seizures, frontal lobe epilepsy, febrile seizures, infantile spasms, juvenile myoclonic epilepsy, Lennox-Gastaut syndrome, Landau-Kleffner Syndrome, myoclonic seizures, mitochondrial disorders associated with seizures, Lafora Disease, progressive myoclonic epilepsies, reflex epilepsy, and Rasmussen's syndrome. There are also numerous types of seizures including simple partial seizures, complex partial seizures, generalized seizures, secondarily generalized seizures, temporal lobe seizures, tonic-clonic seizures, tonic seizures, psychomotor seizures, limbic seizures, status epilepticus, refractory status epilepticus or super-refractory status epilepticus, abdominal seizures, akinetic seizures, autonomic seizures, massive bilateral myoclonus, drop seizures, focal seizures, gelastic seizures, Jacksonian march, motor seizures, multifocal seizures, neonatal seizures, nocturnal seizures, photosensitive seizure, sensory seizures, sylvan seizures, withdrawal seizures and visual reflex seizures.

As used herein, the term "schizophrenia" has its general meaning in the art and represents a group of neuropsychiatric disorders characterized by dysfunctions of the thinking process, such as delusions, hallucinations, and extensive withdrawal of the patient's interests from other people. Approximately one percent of the worldwide population is afflicted with schizophrenia, and this disorder is accompanied by high morbidity and mortality rates.

As used herein, the term "Parkinson's disease" or "PD" has its general meaning in the art and refers to a neurodegenerative disease especially affecting the dopaminergic neurons of the substantia nigra—pars *compacta* and its nigrostriatal projections. As used herein the terms "Parkinson's disease", "Parkinson's" and "Parkinsonism" are to be understood to include the various forms of the condition including idiosyncratic Parkinson's disease, post-encephalitic Parkinson's disease, drug induced Parkinson's disease, such as neuroleptic induced Parkinsonism, and post-ischemic Parkinsonism.

As used herein, the term "hypertension" describes a condition in which an abnormally high arterial blood pressure is present; in a young adult, a hypertensive state is present usually when the diastolic blood pressure is greater than 90 mm Hg and the systolic blood pressure is greater than about 135 to 140 mm Hg.

As used herein, the term "Fragile X syndrome" has its general meaning in the art and refers to the most common inherited form of mental retardation, affecting about 1 in every 4000 boys and about 1 in every 8000 girls. Fragile X syndrome (FXS) is a genetic disorder caused by the expansion of a CGG trinucleotide repeat in the 5' untranslated region (5'-UTR) of the Fragile X mental retardation 1 (FMR1) gene, which is located on the X chromosome. The mutation results in a reduced or absent expression of the Fragile X mental retardation protein (FRMP). Major symptoms associated with FXS are mental retardation and learning disabilities, in particular delays in learning how to sit, walk and talk. As a consequence, FXS patients usually present nervous or cluttered speech. Moreover, FXS patients may have deficient central executive, working, phonological and/or visual-spatial memories; or difficulty with face encoding. Behavioral and emotional problems may also be encountered, such as, for example, hyperactivity, stereotypy, anxiety, seizures, impaired social behavior, cognitive delay, irritability, aggression or self-injurious behavior. Moreover, FXS may also cause ophthalmologic problems including strabismus, and recurrent otitis media and sinusitis during early childhood.

As used herein, the term "autism" denotes a family of disorders of neural development that is characterized by impaired social interaction and communication, restricted and repetitive behaviour accompanied with other deficits. These signs all begin before a child is three years old. Autism affects information processing in the brain by altering how nerve cells and their synapses connect and organize; how this occurs is not well understood. The two other autism spectrum disorders (ASD) are Asperger syndrome, which lacks delays in cognitive development and language, atypical autism, diagnosed when full criteria for the other two disorders are not met, and PDD-NOS when pervasive developmental disorder are not specified.

As used herein, the term "Down syndrome" or "trisomy 21" refers to a chromosomal condition caused by the presence of all or part of a third copy of chromosome 21. It is typically associated with a delay in cognitive ability and physical growth, and a particular set of facial characteristics. Cognitive dysfunction in Down's syndrome patients is correlated with reduced dendritic branching and complexity, along with fewer spines of abnormal shape in the cortical neurons (Martinez de Lagran, M. et al, Cereb Cortex 2012, 22(12): 2867-77).

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the terms "polynucleotide" and "nucleic acid" have their general meaning in the art and refer to a DNA or RNA molecule. However, the terms capture sequences that include any of the known base analogues of DNA and RNA such as, but not limited to 4-acetyl cytosine, 8-hydroxy-N6-methyladenosine, aziridinylcytosine, pseudoisocytosine, 5-(carboxyhydroxylmethyl) uracil, 5-fiuorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxy amino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

As used the term "miR", "microRNA" or "miRNA" has its general meaning in the art and refers to short, non-coding RNA sequences of the length of 15-30 nucleotides found in eukaryotes that are involved in RNA-based gene regulation.

As used herein, the terms "artificial miRNA" or "amiR" refer to a nucleic acid sequence encoding a pri-miRNA scaffold; a nucleic acid sequence encoding a guide strand; and, a nucleic acid sequence encoding a passenger strand, wherein, the pri-miRNA scaffold is derived from a naturally-occurring pri-miRNA and comprises at least one flanking sequence and a loop-forming sequence comprising at least 4 nucleotides. Different amiRs sequences are constructed by replacing the 21-22 nucleotide guide strand (the antisense targeting sequence) of a naturally-occurring pri-microRNA scaffold.

In some embodiments, the guide strand of an amiR and the passenger strand of an amiR share at least 50% complementarily to NKCC1 nucleic acid sequence but are not 100% complementary to one another. In some embodiments, the nucleic acid sequence encoding the guide strand and the nucleic acid sequence encoding the passenger strand are inserted into the pri-miRNA scaffold between the flanking sequence and the loop-forming sequence, thereby forming a stem.

In some embodiments, the nucleic acid sequence encoding the guide strand of an amiR and the nucleic acid sequence encoding the passenger strand of an amiR have at least one base pair mismatch. In some embodiments, the nucleic acid sequence encoding the guide strand and the nucleic acid sequence encoding the passenger strand have two base pair mismatches, three base pair mismatches, four base pair mismatches, five base pair mismatches, six base pair mismatches, seven base pair mismatches, eight base pair mismatches, nine base pair mismatches, ten base pair mismatches, eleven base pair mismatches, twelve base pair mismatches, thirteen base pair mismatches, fourteen base pair mismatches or fifteen base pair mismatches. In some embodiments, the nucleic acid sequence encoding the guide strand and the nucleic acid sequence encoding the passenger strand have mismatches at no more than ten consecutive base pairs. In some embodiments, at least one base pair mismatch is located at an anchor position. In some embodiments, at least one base pair mismatch is located in a center portion of the stem.

In some embodiments, the amiR scaffold of the present invention consists of a 5' flanking region derived from a natural miRNA (for example from the mouse miRNA-155, sequence: tggaggcttgctgaaggctgtatgct; SEQ ID NO:90), a TGCT nucleotide overhang, a 5'G+the short 21 nucleotide antisense sequence (guide strand) derived from the hNKCC1 selected from the group consisting of SEQ ID NOs:4, 8, 15, 16, 18, 23, 25, 39, 40, 44, 45, 53, 57, 64, 66, 67, 68, 69, 82 and 88, a loop forming sequence (for example: GTTTTGGCCACTGACTGAC; SEQ ID NO:91), a short 19 nucleotides sense sequence (passenger strand) derived from hNKCC1 with 2 nucleotides removed (42) to create an internal loop, a CAGG overhang and a 3' flanking region derived from a natural miRNA (for example from the mouse miRNA-155, sequence: caggacacaaggcctgttactagcactcacatggaacaaatggccc; SEQ ID NO:92). Such a construct is described in the U.S. Patent Publication No. 2004/0053876 and is depicted in FIG. 1. In some embodiments, the amiR scaffold is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

As used herein, the term "vector" has its general meaning in the art and refers to a plasmid, virus or other vehicle that can be manipulated by insertion or incorporation of a polynucleotide. The vector of the present invention is used for genetic manipulation, to introduce/transfer polynucleotides into cells, and to transcribe or translate the inserted polynucleotide in cells. A vector generally contains at least an origin of replication for propagation in a cell and expression control element (e.g. a promoter). Control elements, including expression control elements as set forth herein, present within a vector are included to facilitate proper transcription and if appropriate translation (e.g. splicing signal for introns, maintenance of the correct reading frame of the gene to permit in-frame translation of mRNA and, stop codons, etc.).

Typically, the vector is a non-viral vector or a viral vector. Large numbers of suitable vectors are known to those of skill in the art, and are commercially available. Non-viral vectors typically rely on a plasmid-based gene delivery system, where only the naked DNA is delivered, potentially in conjunction with physicochemical methods that facilitate transfection. In some embodiments, the viral vector is an adeno-associated virus, a retrovirus, bovine papilloma virus, an adenovirus vector, a lentiviral vector, a vaccinia virus, a polyoma virus, or an infective virus. Retroviruses may be chosen as gene delivery vectors due to their ability to integrate their genes into the host genome, transferring a large amount of foreign genetic material, infecting a broad spectrum of species and cell types and for being packaged in special cell-lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV 1, HIV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g. U.S. Pat. Nos. 6,013,516 and 5,994,136, both of which are incorporated herein by reference. In general, the vectors are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. In some embodiments, the vector is an AAV vector. As used herein the term "AAV" refers to the more than 30 naturally occurring and available adeno-associated viruses, as well as artificial AAVs. Typically, the AAV capsid, ITRs, and other selected AAV components described herein, may be readily selected from among any AAV, including, without limitation, AAV1, AAV2, AAV3, AAV4, AAV5, AAV6, AAV6.2, AAV7, AAV8, AAV9, rh10, AAVrh64R1, AAVrh64R2, rh8, rh74, AAV-DJ, AAV2g9, variants of any of the known or mentioned AAVs or AAVs yet to be discovered or variants or mixtures thereof. The genomic sequences of various serotypes of AAV, as well as the sequences of the native terminal repeats (TRs), Rep proteins, and capsid subunits including VP1 protein are known in the art. Such sequences may be found in the literature or in public databases such as GenBank. See, e.g., GenBank Accession Numbers NC_002077 (AAV-1), AF063497 (AAV-1), NC_001401 (AAV-2), AF043303 (AAV-2), NC_001729 (AAV-3), NC_001829 (AAV-4), U89790 (AAV-4), NC_006152 (AAV-5), AF513851 (AAV-7), AF513852 (AAV-8), and NC_006261 (AAV-8); the disclosures of which are incorporated by reference herein for teaching AAV nucleic acid and amino acid sequences. See also, e.g., Srivistava et al. (1983) J. Virology 45:555; Chiorini et al. (1998) J. Virology 71:6823; Chiorini et al. (1999) J. Virology 73: 1309; Bantel-Schaal et al. (1999) J. Virology 73:939; Xiao et al. (1999) J. Virology 73:3994; Muramatsu et al. (1996) Virology 221:208; Shade et al., (1986) J. Virol. 58:921; Gao et al. (2002) Proc. Nat. Acad. Sci. USA 99: 11854; Moris et al. (2004) Virology 33:375-383; international patent publications WO 00/28061, WO 99/61601, WO 98/11244; and U.S. Pat. No. 6,156,303. The recombinant AAV vector of the present invention typically comprises 5' and 3' adeno-associated virus inverted terminal repeats (ITRs), the polynucleotide of interest (i.e a heterologous polynucleotide) operatively linked to a promoter. The vectors of the invention are produced using methods known in the art. In short, the methods generally involve (a) the introduction of the AAV vector into a host cell, (b) the introduction of an AAV helper construct into the host cell, wherein the helper construct comprises the viral functions missing from the AAV vector and (c) introducing a helper virus into the host cell. All functions for AAV virion replication and packaging need to be present, to achieve replication and packaging of the AAV vector into AAV virions. The introduction into the host cell can be carried out using standard virological techniques simultaneously or sequentially. Finally, the host cells are cultured to produce AAV virions and are purified using standard techniques such as CsCl gradients or column chromatography. Residual helper virus activity can be inactivated using known methods, such as for example heat inactivation. The purified AAV virion is then ready for use in the methods.

Typically, the vector of the present invention include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence, is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters". Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1 a promoter [Invitrogen]. In some embodiments, neuronal specific promoters are used. Exemplary neuronal specific promoters include, but are not limited to the following: synapsin-1 (Syn) promoter, neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, the vector of the present invention is delivered in the hippocampus of the subject. In some embodiments, the vector of the present invention is delivered to the subject by intravenous injection. In some embodiments, the vector of the present invention is delivered by intrathecal administration. As used herein the term "intrathecal administration" refers to the administration of the vector into the spinal canal. For example, intrathecal administration may comprise injection in the cervical region of the spinal canal, in the thoracic region of the spinal canal, or in the lumbar region of the spinal canal. Typically, intrathecal administration is performed by injecting the vector into the subarachnoid cavity (subarachnoid space) of the spinal canal, which is the region between the arachnoid membrane and pia mater of the spinal canal. The subarachnoid space is occupied by spongy tissue consisting of trabeculae (delicate connective tissue filaments that extend from the arachnoid mater and blend into the pia mater) and intercommunicating channels in which the cerebrospinal fluid is contained. In some embodiment, the vector of the present invention is delivered by intraventricular administration. As used herein the term "intraventricular administration" refers to the administration of the vector into a ventricular region of the forebrain of the subject.

In some embodiments, the effective amount is a therapeutically effective amount. By a "therapeutically effective amount" is meant a sufficient amount of the vector to treat the disease at a reasonable benefit/risk ratio. It will be understood that the total daily usage of the vector will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. Thus, the doses of vectors may be adapted depending on the disease condition, the subject (for example, according to his weight, metabolism, etc.), the treatment schedule, etc. A preferred effective dose within the context of this invention is a dose allowing an optimal transduction. Typically, from $10^8$ to $10^{12}$ viral genomes (vg) are administered per dose in mice. Typically, the doses of AAV vectors to be administered in humans may range from $10^{10}$ to $10^{14}$ vg.

The vector of the invention is formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient (i.e. the vector of the invention). The precise nature of the carrier or other material may be determined by the skilled person according to the route of administration. The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. For injection, the active ingredient will be in the form of an aqueous solution, which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. For delayed release, the vector may be included in a pharmaceutical composition, which is formulated for slow release, such as in microcapsules formed from biocompatible polymers or in liposomal carrier systems according to methods known in the art. Typically, the pharmaceutical composition of the present invention is supplied in a prefilled syringe. A "ready-to-use syringe" or "prefilled syringe" is a syringe which is supplied in a filled state, i.e. the pharmaceutical composition to be administered is already present in the syringe and ready for administration. Prefilled syringes have many benefits compared to separately provided syringe and vial, such as improved convenience, affordability, accuracy, sterility, and safety. The use of prefilled syringes results in greater dose precision, in a reduction of the potential for needle sticks injuries that can occur while drawing medication from vials, in pre-measured dosage reducing dosing errors due to the need to reconstituting and/or drawing medication into a syringe, and in less overfilling of the syringe helping to reduce costs by minimising drug waste. In some embodiments the pH of the liquid pharmaceutical composition of the present invention is in the range of 5.0 to 7.0, 5.1 to 6.9, 5.2 to 6.8, 5.3 to 6.7 or 5.4 to 6.6.

EXAMPLE 1

In Ts65Dn neurons, the intracellular chloride concentration is elevated leading to depolarizing and possibly excitatory actions of GABA. We design an RNAi strategy with amiR to reduce the expression of NKCC1 in neurons. Using primary neuronal cultures from Ts65Dn mice, a well-known mouse model of Down syndrome, we found that our amiR strategy with viral vectors was able to reduce the expression of NKCC1 protein. Reducing NKCC1 protein expression by amiR restored the inhibitory action of GABA in Ts65Dn neurons similar to wild type (WT) neurons. Furthermore, we found that in vivo viral delivery of amiR molecules in the hippocampus of Ts65Dn mice rescued the cognitive deficits in four different behavioral tests for learning and memory. This approach is therefore efficient in vitro and in vivo to restore physiological activity and behavioral parameters in DS.

EXAMPLE 2 amiR sequences reported in Table B are all predicted based on the human NKCC1 (hNKCC1) DNA sequence (NM_001046.2) by using the online tool BLOCK-iT™ RNAi Designer (algorithm 1, TABLE A). By using 8 additional algorithms (algorithms 2-9, listed in TABLE A), we predicted a number of additional RNAi sequences that in some case corresponded to those reported in table B obtained with algorithm 1. Each of the sequences predicted by algorithm 1 (TABLE B) was scored based on the number of times these sequences ±4 nucleotides was predicted by the algorithms 2-9. Therefore, sequences listed in TABLE B have the highest probability to bind and silence NKCC1.

EXAMPLE 3

Figure 6:
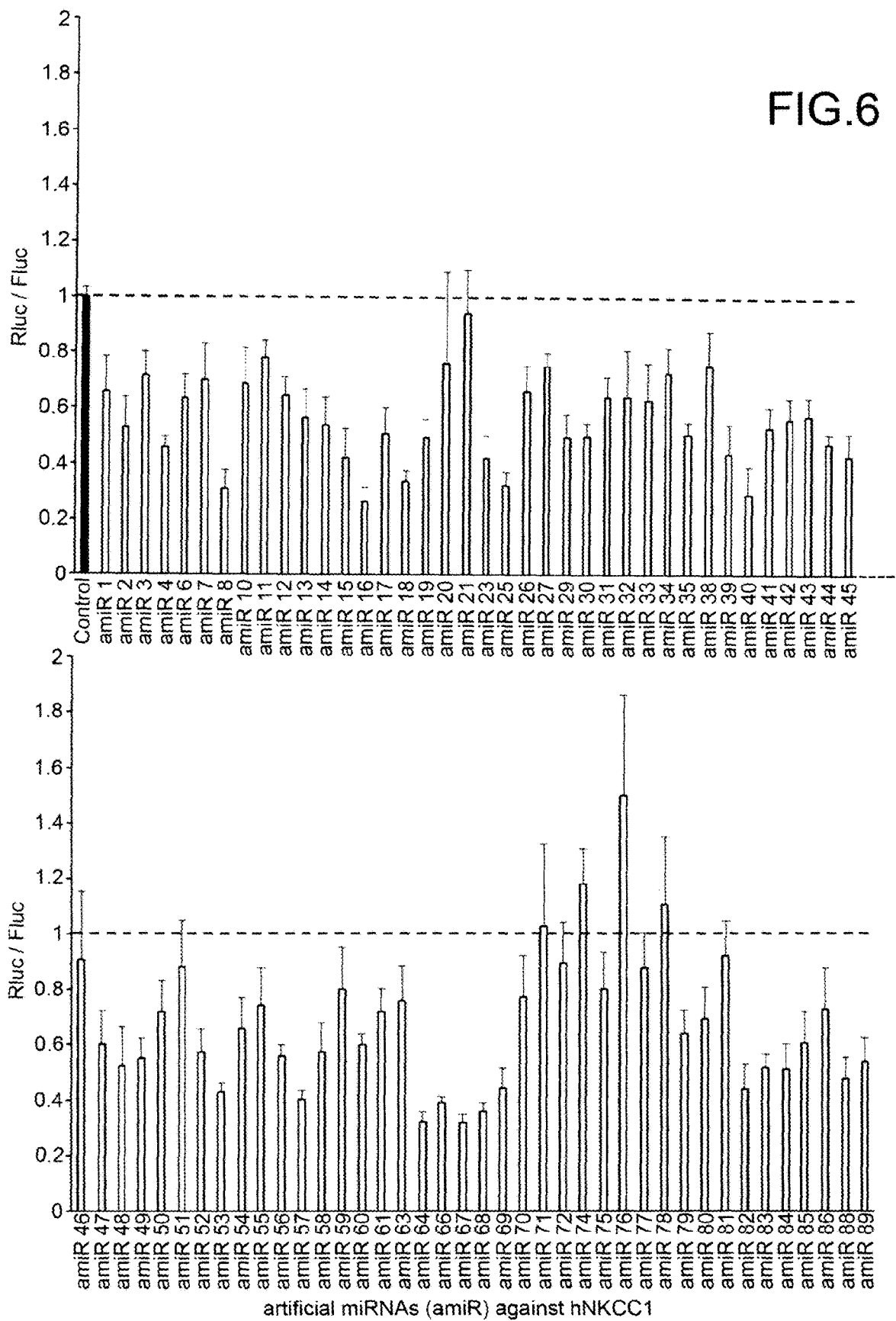
FIG. 6 represents the effect of different amiR molecules against human NKCC1 (hNKCC1) on the Rluc/Fluc ratio of the dual luciferase hNKCC1 sensor plasmid of FIG. 6. Control samples were transfected with hNKCC1 sensor plasmid and control amiR sequence. Histograms represent average ±SEM.

The silencing efficacy of 78 out of 89 amiR sequences reported in Table B against hNKCC1 was evaluated with a dual-luciferase hNKCC1 sensor (FIGS. 6 and 7). Human H293T kidney cells were grown in 96-well plates and transfected with each amiR sequence together with hNKCC1 dual-luciferase plasmid sensor with Lipofectamnine2000 (Thermo). After 48 hours the ratio between *Renilla* luciferase (RLuc) and Firefly luciferase (FLuc) was measured with Dual-luciferase assay (Promega) on a Victor3 multiplate reader (PerkinElmer). For each transfected amiR sequence the decrease in RLuc/FLuc ratio with respect to samples transfected with control amiR plasmid indicates the degree of hNKCC1 knockdown. The silencing activity of different amiR sequences against hNKCC1, expressed as average RLuc/Fluc ratio (obtained from 4 independent transfections), is reported in TABLE C, together with the corresponding P value obtained with Student's t-test versus samples transfected with control amiR plasmid.

EXAMPLE 4

The different amiR sequences against hNKCC1 reported in Table B were also evaluated for the number of possible off-target genes predicted with the freely-accessible microRNA prediction tool TargetScan (Agarwal et al., Elife.12: 4 (2015)). Off-target prediction was evaluated on full length-transcript sequences (coding sequence plus 3' untranslated region) for all annotated human genes (ENSEMBL release GRCh38). Table D shows the number of possible off-target genes for each of the amiR sequences. The list is sorted from the lowest to the highest number of possible off-target genes and also reports the corresponding silencing activity from TABLE C. Therefore, the sequences listed on top of TABLE D have the highest activity to silence NKCC1 with the lowest off-target probability.

TABLE A

Description of the algorithms used for the prediction of RNAi sequences in hNKCC1.

| PREDICTION | ALGORITHM |
|---|---|
| 1 | BLOCK-iT ™ RNAi Designer for miRNAi (Thermo Fisher) |
| 2 | siDESIGN Center (Dharmacon) |
| 3 | Custom Dicer-Substrate siRNA prediction tool (IDT technologies) |
| 4 | siRNA target finder (Genscript) |
| 5 | i-score designer |
| 6 | siRNA Wizard v3.1 |
| 7 | RNAi Target Sequence Selector |
| 8 | DSIR Designer of Small Interfering RNA |
| 9 | OligoWalk |

TABLE B

Scoring of amiR sequences predicted by BLOCK-iT ™ RNAi Designer.

| aSCORE | bSTART | amiR SEQUENCE (reverse complement of NKCC1 sense) | cBlast | SEQ ID NO: |
|---|---|---|---|---|
| 9 | 3009 | TTCCACACTTACTACCACATC |  | 1 |
| 8 | 2852 | TACATATCCACATCCCTCATA | Mac | 2 |
| 8 | 2854 | TATACATATCCACATCCCTCA | Mac | 3 |
| 8 | 3008 | TCCACACTTACTACCACATCC | Mac | 4 |
| 8 | 3011 | TATTCCACACTTACTACCACA |  | 5 |
| 8 | 3601 | TTAACCTGATCTGCCGGTATG |  | 6 |
| 7 | 1330 | TAAGCAACTCCACCACGGTTT |  | 7 |
| 7 | 2849 | ATATCCACATCCCTCATATCT | Mac | 8 |
| 7 | 2853 | ATACATATCCACATCCCTCAT | Mac | 9 |
| 7 | 3010 | ATTCCACACTTACTACCACAT |  | 10 |
| 7 | 3012 | ATATTCCACACTTACTACCAC |  | 11 |
| 7 | 3600 | TAACCTGATCTGCCGGTATGT |  | 12 |
| 7 | 3603 | ATTTAACCTGATCTGCCGGTA | Mac | 13 |
| 7 | 3780 | TGAATAGAAGGTAAGGACACT |  | 14 |
| 7 | 3781 | ATGAATAGAAGGTAAGGACAC |  | 15 |
| 6 | 1113 | TACAAGGACTGATAGACCTAT | Mac | 16 |
| 6 | 1114 | TTACAAGGACTGATAGACCTA | Mac | 17 |
| 6 | 1115 | ATTACAAGGACTGATAGACCT | Mac | 18 |
| 6 | 1331 | TTAAGCAACTCCACCACGGTT |  | 19 |
| 6 | 2472 | ACGAATTGAATGCTGCAGTGC | Mac | 20 |
| 6 | 3558 | CTCATTATCTGTTATTCGCCA | Mac | 21 |
| 6 | 3778 | AATAGAAGGTAAGGACACTCT |  | 22 |
| 5 | 1023 | TACTAATACACCCTTGATCCA | Mac | 23 |
| 5 | 1167 | TATTGCTGAAGTAGACAATCC | Mus + Mac | 24 |
| 5 | 1304 | AATCCAACCACATACATAGCA | Mac | 25 |
| 5 | 1335 | TTCCTTAAGCAACTCCACCAC | Mac | 26 |
| 5 | 2469 | AATTGAATGCTGCAGTGCATT | Mac | 27 |
| 5 | 2847 | ATCCACATCCCTCATATCTGC | Mac | 28 |
| 5 | 2848 | TATCCACATCCCTCATATCTG | Mac | 29 |
| 5 | 3006 | CACACTTACTACCACATCCTT | Mac | 30 |
| 5 | 3116 | TTCAACAGTGGTTGAGTTGCA | Mac | 31 |
| 5 | 3371 | AGCAAAGTAGCCATCGCTCTC | Mac | 32 |
| 5 | 3372 | AAGCAAAGTAGCCATCGCTCT | Mac | 33 |
| 5 | 3373 | TAAGCAAAGTAGCCATCGCTC | Mac | 34 |
| 5 | 3379 | ACTTGCTAAGCAAAGTAGCCA | Mac | 35 |
| 5 | 3380 | AACTTGCTAAGCAAAGTAGCC | Mac | 36 |
| 5 | 3599 | AACCTGATCTGCCGGTATGTC |  | 37 |
| 4 | 978 | TTCTGCAGTATACGTGACCAC |  | 38 |
| 4 | 1029 | ACAACGTACTAATACACCCTT | Mac | 39 |
| 4 | 1032 | CATACAACGTACTAATACACC | Mac | 40 |
| 4 | 1337 | TGTTCCTTAAGCAACTCCACC | Mac | 41 |
| 4 | 1715 | AGGAGTGTTCCTTTGGGTATG | Mac | 42 |
| 4 | 1716 | TAGGAGTGTTCCTTTGGGTAT | Mac | 43 |
| 4 | 1717 | CTAGGAGTGTTCCTTTGGGTA | Mac | 44 |
| 4 | 1770 | AGAACCTACAGATACTGCAAT | Mac | 45 |
| 4 | 1805 | TCATTAACGTTTCCAGTGGCA | Mac | 46 |
| 4 | 1807 | TGTCATTAACGTTTCCAGTGG | Mac | 47 |
| 4 | 1940 | AATCCTGACACCATACTCATT | Mac | 48 |
| 4 | 1941 | AAATCCTGACACCATACTCAT | Mac | 49 |
| 4 | 2005 | TCACTAGGGATGCTAATGCTG |  | 50 |
| 4 | 2381 | TACAGCCCAAGGACTATCACA |  | 51 |
| 4 | 2383 | TATACAGCCCAAGGACTATCA |  | 52 |
| 4 | 2475 | AAGACGAATTGAATGCTGCAG | Mac | 53 |
| 4 | 2642 | TTCATGGCTTGTCTTCGAGGA | Mac | 54 |
| 4 | 2643 | TTTCATGGCTTGTCTTCGAGG | Mac | 55 |
| 4 | 2832 | ATCTGCTTGCAACCAATCTTT | Mac | 56 |

TABLE B-continued

Scoring of amiR sequences predicted by BLOCK-iT™ RNAi Designer.

| aSCORE | bSTART | amiR SEQUENCE (reverse complement of NKCC1 sense) | cBlast | SEQ ID NO: |
|---|---|---|---|---|
| 4 | 2834 | ATATCTGCTTGCAACCAATCT | Mac | 57 |
| 4 | 2835 | CATATCTGCTTGCAACCAATC | Mac | 58 |
| 4 | 3113 | AACAGTGGTTGAGTTGCAGTC | Mac | 59 |
| 4 | 3377 | TTGCTAAGCAAAGTAGCCATC | Mac | 60 |
| 4 | 3555 | ATTATCTGTTATTCGCCATGG | Mac | 61 |
| 4 | 3560 | AGCTCATTATCTGTTATTCGC |  | 62 |
| 3 | 755 | TGGGTATCATAATAGTAGTGC | Mac | 63 |
| 3 | 756 | GTGGGTATCATAATAGTAGTG | Mac | 64 |
| 3 | 1098 | ACCTATTCCAGCTTGACCCAC | Mac | 65 |
| 3 | 1267 | CAAAGGCGAAGATTAGACCAA | Mac | 66 |
| 3 | 1405 | AAAGAATCACGACTGTAATGG |  | 67 |
| 3 | 1776 | AACACAAGAACCTACAGATAC | Mac | 68 |
| 3 | 1836 | AGTACAGTTTGTTAGCTCTGT |  | 69 |
| 3 | 1855 | TTAATTTGCAGGCTGCAGAAG | Mac | 70 |
| 3 | 2015 | TTGGGAGCACTCACTAGGGAT |  | 71 |
| 3 | 2016 | TTTGGGAGCACTCACTAGGGA |  | 72 |
| 3 | 2207 | AATGCATATGATGCAAGGAAG | Mac | 73 |
| 3 | 2460 | CTGCAGTGCATTCAGGTAAGT | Mac | 74 |
| 3 | 2462 | TGCTGCAGTGCATTCAGGTAA | Mac | 75 |
| 3 | 2467 | TTGAATGCTGCAGTGCATTCA | Mac | 76 |
| 3 | 2647 | TCTCTTTCATGGCTTGTCTTC | Mac | 77 |
| 3 | 2666 | TTGGCTTGATCGATGGACATC | Mac | 78 |
| 3 | 3105 | TTGAGTTGCAGTCTTGCCATC | Mac | 79 |
| 3 | 3117 | TTTCAACAGTGGTTGAGTTGC | Mac | 80 |
| 3 | 3381 | GAACTTGCTAAGCAAAGTAGC | Mac | 81 |
| 3 | 3392 | AAGTCTATCCGGAACTTGCTA |  | 82 |
| 3 | 3608 | AACTCATTTAACCTGATCTGC |  | 83 |
| 3 | 3705 | TAACCATGCCATGTAGAGAGC | Mac | 84 |
| 3 | 3708 | TTCTAACCATGCCATGTAGAG | Mac | 85 |
| 2 | 1705 | CTTTGGGTATGGCTGACTGAG | Mus | 86 |
| 2 | 1708 | TTCCTTTGGGTATGGCTGACT | Mus | 87 |
| 2 | 1293 | ATACATAGCAACTGCAACAGC | Mac | 88 |
| 2 | 2047 | AGATGTTGTCCTTACATAGAG | Mac | 89 | a each sequence was scored based on the number of times that a certain amiR sequence ± 4 nucleotides was predicted by the algorithms 2-9 (TABLE A).
b Position of the first nucleotide of each amiR sequence in the hNKCC1 sequence (NCBI references sequence NM_001046; SEQUENCE XX of the patient).
c blast prediction of the homology of the amiR sequence with *Macaca Fascicularis* (Mac) and *Mus Musculus* (Mus) NKCC1 sequences (NCBI references sequences XM_005557674 and NM_009194 respectively).

TABLE C

Screening of amiRs sequence silencing activity with hNKCC1 dual-luciferase plasmid sensor. Each amiR sequence was transfected in human H293T kidney cells together with hNKCC1 dual-luciferase plasmid sensor. After 48 hours the ratio between Renilla luciferase (RLuc) and Firefly luciferase (FLuc) was measured. For each transfected amiR sequence the decrease in RLuc/FLuc ratio with respect to samples transfected with control amiR plasmid indicates the degree of hNKCC1 knockdown.

| Sequence | Rluc/Fluc ratio | T test P value |
|---|---|---|
| Control | 1.00 | not tested |
| amiR 1 | 0.66 | 0.00568323 |
| amiR 2 | 0.53 | 0.00010958 |
| amiR 3 | 0.72 | 0.00326969 |
| amiR 4 | 0.46 | 0.00000164 |
| amiR 5 | N/A | N/A |
| amiR 6 | 0.63 | 0.00042794 |
| amiR 7 | 0.70 | 0.00813742 |
| amiR 8 | 0.31 | 0.00000030 |
| amiR 9 | N/A | N/A |
| amiR 10 | 0.69 | 0.00545553 |
| amiR 11 | 0.78 | 0.04243644 |
| amiR 12 | 0.65 | 0.00031859 |
| amiR 13 | 0.57 | 0.00016529 |
| amiR 14 | 0.54 | 0.00009203 |
| amiR 15 | 0.42 | 0.00000983 |
| amiR 16 | 0.26 | 0.00000006 |
| amiR 17 | 0.51 | 0.00003684 |
| amiR 18 | 0.34 | 0.00000016 |
| amiR 19 | 0.49 | 0.00001809 |
| amiR 20 | 0.76 | 0.11578695 |
| amiR 21 | 0.94 | 0.60443038 |
| amiR 22 | N/A | N/A |
| amiR 23 | 0.42 | 0.00000319 |
| amiR 24 | N/A | N/A |
| amiR 25 | 0.32 | 0.00000018 |
| amiR 26 | 0.66 | 0.00097331 |
| amiR 27 | 0.75 | 0.00370223 |
| amiR 28 | N/A | N/A |
| amiR 29 | 0.50 | 0.00001916 |
| amiR 30 | 0.50 | 0.00000618 |
| amiR 31 | 0.64 | 0.00034731 |
| amiR 32 | 0.64 | 0.00680754 |
| amiR 33 | 0.63 | 0.00216182 |
| amiR 34 | 0.73 | 0.00542337 |
| amiR 35 | 0.51 | 0.00000619 |
| amiR 36 | N/A | N/A |
| amiR 37 | N/A | N/A |
| amiR 38 | 0.76 | 0.02141786 |
| amiR 39 | 0.44 | 0.00001562 |
| amiR 40 | 0.29 | 0.00000080 |
| amiR 41 | 0.53 | 0.00003131 |
| amiR 42 | 0.57 | 0.00005630 |
| amiR 43 | 0.58 | 0.00005757 |
| amiR 44 | 0.47 | 0.00000221 |
| amiR 45 | 0.43 | 0.00000448 |
| amiR 46 | 0.91 | 0.45875369 |
| amiR 47 | 0.60 | 0.00069596 |
| amiR 48 | 0.52 | 0.00031816 |
| amiR 49 | 0.55 | 0.00003857 |
| amiR 50 | 0.72 | 0.00754464 |
| amiR 51 | 0.88 | 0.30771639 |
| amiR 52 | 0.57 | 0.00009937 |
| amiR 53 | 0.43 | 0.00000076 |

TABLE C-continued

Screening of amiRs sequence silencing activity with hNKCC1 dual-luciferase plasmid sensor. Each amiR sequence was transfected in human H293T kidney cells together with hNKCC1 dual-luciferase plasmid sensor. After 48 hours the ratio between Renilla luciferase (RLuc) and Firefly luciferase (FLuc) was measured. For each transfected amiR sequence the decrease in RLuc/FLuc ratio with respect to samples transfected with control amiR plasmid indicates the degree of hNKCC1 knockdown.

| Sequence | Rluc/Fluc ratio | T test P value |
| --- | --- | --- |
| amiR 54 | 0.66 | 0.00200294 |
| amiR 55 | 0.74 | 0.02008219 |
| amiR 56 | 0.56 | 0.00001822 |
| amiR 57 | 0.40 | 0.00000045 |
| amiR 58 | 0.57 | 0.00022920 |
| amiR 59 | 0.80 | 0.07457806 |
| amiR 60 | 0.60 | 0.00004354 |
| amiR 61 | 0.72 | 0.00342161 |
| amiR 62 | N/A | N/A |
| amiR 63 | 0.76 | 0.03542429 |
| amiR 64 | 0.32 | 0.00000011 |
| amiR 65 | N/A | N/A |
| amiR 66 | 0.39 | 0.00000029 |
| amiR 67 | 0.31 | 0.00000009 |
| amiR 68 | 0.36 | 0.00000018 |
| amiR 69 | 0.44 | 0.00000349 |
| amiR 70 | 0.77 | 0.04328713 |
| amiR 71 | 1.03 | 0.86591981 |
| amiR 72 | 0.89 | 0.31421373 |
| amiR 73 | N/A | N/A |
| amiR 74 | 1.18 | 0.07392157 |
| amiR 75 | 0.80 | 0.05885524 |
| amiR 76 | 1.50 | 0.02903011 |
| amiR 77 | 0.88 | 0.21801829 |
| amiR 78 | 1.10 | 0.48846883 |
| amiR 79 | 0.64 | 0.00044779 |
| amiR 80 | 0.69 | 0.00439795 |
| amiR 81 | 0.92 | 0.40010019 |
| amiR 82 | 0.44 | 0.00000685 |
| amiR 83 | 0.51 | 0.00000802 |
| amiR 84 | 0.51 | 0.00003236 |
| amiR 85 | 0.61 | 0.00055635 |
| amiR 86 | 0.72 | 0.01859616 |
| amiR 87 | N/A | N/A |
| amiR 88 | 0.47 | 0.00000950 |
| amiR 89 | 0.54 | 0.00004965 |

Based on the data reported in Table C, the amiR sequences which are more effective in hNKCC1 knockdown are SEQ ID NOs:4, 8, 15, 16, 18, 23, 25, 39, 40, 44, 45, 53, 57, 64, 66, 67, 68, 69, 82 and 88.

TABLE D

Prediction of amiRs possible off-target genes. Each amiR sequence was evaluated with TargetScan software for the possible number of off-target genes on all annotated human transcripts. The table also shows the silencing activity from Table C. The table is sorted from the lowest to the highest number of possible off-target genes detected.

| amiRs | Predicted off-target sites | Rluc/Fluc ratio |
| --- | --- | --- |
| amiR-53 | 148 | 0.43 |
| amiR-20 | 178 | 0.76 |
| amiR-39 | 187 | 0.44 |
| amiR-66 | 213 | 0.39 |
| amiR-82 | 530 | 0.44 |
| amiR-45 | 594 | 0.43 |
| amiR-37 | 622 | N/A |
| amiR-25 | 633 | 0.32 |
| amiR-63 | 644 | 0.76 |
| amiR-85 | 685 | 0.61 |
| amiR-43 | 706 | 0.58 |
| amiR-50 | 729 | 0.72 |
| amiR-65 | 737 | N/A |
| amiR-81 | 785 | 0.92 |
| amiR-64 | 787 | 0.32 |
| amiR-7 | 790 | 0.70 |
| amiR-84 | 799 | 0.51 |
| amiR-6 | 804 | 0.63 |
| amiR-51 | 823 | 0.88 |
| amiR-52 | 831 | 0.57 |
| amiR-12 | 833 | 0.65 |
| amiR-44 | 852 | 0.47 |
| amiR-2 | 883 | 0.53 |
| amiR-23 | 924 | 0.42 |
| amiR-60 | 926 | 0.60 |
| amiR-15 | 934 | 0.42 |
| amiR-40 | 958 | 0.29 |
| amiR-76 | 961 | 1.50 |
| amiR-8 | 963 | 0.31 |
| amiR-30 | 964 | 0.50 |
| amiR-48 | 976 | 0.52 |
| amiR-49 | 996 | 0.55 |
| amiR-22 | 1018 | N/A |
| amiR-79 | 1028 | 0.64 |
| amiR-17 | 1030 | 0.51 |
| amiR-88 | 1059 | 0.47 |
| amiR-14 | 1072 | 0.54 |
| amiR-67 | 1073 | 0.31 |
| amiR-58 | 1078 | 0.57 |
| amiR-57 | 1081 | 0.40 |
| amiR-5 | 1101 | N/A |
| amiR-68 | 1118 | 0.36 |
| amiR-35 | 1124 | 0.51 |
| amiR-36 | 1125 | N/A |
| amiR-73 | 1157 | N/A |
| amiR-46 | 1186 | 0.91 |
| amiR-16 | 1188 | 0.26 |
| amiR-71 | 1207 | 1.03 |
| amiR-42 | 1218 | 0.57 |
| amiR-83 | 1229 | 0.51 |
| amiR-24 | 1250 | N/A |
| amiR-27 | 1301 | 0.75 |
| amiR-29 | 1349 | 0.50 |
| amiR-33 | 1353 | 0.63 |
| amiR-59 | 1364 | 0.80 |
| amiR-69 | 1369 | 0.44 |
| amiR-78 | 1388 | 1.10 |
| amiR-47 | 1401 | 0.60 |
| amiR-86 | 1405 | 0.72 |
| amiR-13 | 1419 | 0.57 |
| amiR-62 | 1502 | N/A |
| amiR-19 | 1517 | 0.49 |
| amiR-54 | 1615 | 0.66 |
| amiR-55 | 1660 | 0.74 |
| amiR-61 | 1734 | 0.72 |
| amiR-32 | 1785 | 0.64 |
| amiR-18 | 1820 | 0.34 |
| amiR-1 | 1835 | 0.66 |
| amiR-34 | 1863 | 0.73 |
| amiR-31 | 1866 | 0.64 |
| amiR-4 | 1922 | 0.46 |
| amiR-70 | 1987 | 0.77 |
| amiR-11 | 2015 | 0.78 |
| amiR-89 | 2105 | 0.54 |
| amiR-9 | 2122 | N/A |
| amiR-41 | 2137 | 0.53 |
| amiR-26 | 2170 | 0.66 |
| amiR-21 | 2465 | 0.94 |
| amiR-80 | 2590 | 0.69 |
| amiR-3 | 2642 | 0.72 |
| amiR-87 | 2993 | N/A |
| amiR-28 | 3003 | N/A |
| amiR-77 | 3500 | 0.88 |
| amiR-56 | 3565 | 0.56 |
| amiR-38 | 3807 | 0.76 |

TABLE D-continued

Prediction of amiRs possible off-target genes. Each amiR sequence was evaluated with TargetScan software for the possible number of off-target genes on all annotated human transcripts. The table also shows the silencing activity from Table C. The table is sorted from the lowest to the highest number of possible off-target genes detected.

| amiRs | Predicted off-target sites | Rluc/Fluc ratio |
| --- | --- | --- |
| amiR-10 | 3928 | 0.69 |
| amiR-75 | 4183 | 0.80 |
| amiR-74 | 4501 | 1.18 |
| amiR-72 | 5971 | 0.89 |

Based on the data reported in Table D, SEQ ID Nos.: 25, 39, 45, 53, 64, 66 and 82 and are identified as being the most preferred sequences for use in the invention, in that they show the lowest number of possible off-target genes.

The invention claimed is:

1. A method for reducing the expression of NKCC1 in a subject in need thereof, comprising delivering to the subject an effective amount of a vector comprising a polynucleotide encoding an artificial microRNA (amiR) capable of reducing the expression of NKCC1 in the subject, wherein the amiR comprises at least one nucleic acid sequence selected from the group consisting of: SEQ ID NOs: 8, 23, 39, 40, and 67.

2. The method of claim 1, wherein the effective amount of the vector is a therapeutically effective amount.

3. The method of claim 1, wherein the subject suffers from a disease selected from the group consisting of: Down syndrome, Fragile X syndrome, Rett syndrome, Tuberous sclerosis, traumatic brain injury, epilepsy, autism, Schizophrenia, Parkinson's disease and hypertension.

4. The method of claim 1, wherein the amiR consists of a 5' flanking region derived from a natural miRNA, a TGCT nucleotide overhang, a 5'G+the short 21 nucleotide antisense sequence derived from the hNKCC1 selected from the group consisting of SEQ ID NOs: 8, 23, 39, 40, and 67, a loop forming sequence, a short 19 nucleotides sense sequence derived from hNKCC1 with 2 nucleotides removed (42) to create an internal loop, a CAGG overhang and a 3' flanking region derived from a natural miRNA.

5. The method of claim 4, wherein the 5' flanking region derived from a natural miRNA is SEQ ID NO: 90.

6. The method of claim 4, wherein the loop forming sequence is SEQ ID NO: 91.

7. The method claim 4, wherein the 3' flanking region derived from a natural miRNA is SEQ ID NO: 92.

8. The method of claim 1, wherein the vector is a non-viral vector or a viral vector.

9. The method of claim 8, wherein the viral vector is an AAV vector.

10. The method claim 1, wherein the vector comprises a neuronal specific promoter.

11. The method of claim 10, wherein the neuronal specific promoter is selected from the group consisting of: a synapsin-1 (Syn) promoter, a neuron-specific enolase (NSE) promoter, a neurofilament light-chain gene promoter, and a neuron-specific vgf gene promoter.

12. The method of claim 1, which comprises delivering the vector to the hippocampus of the subject.

13. The method of claim 1, which comprises delivering the vector to the subject by intravenous injection.

14. The method of claim 1, which comprises delivering the vector to the subject by intrathecal administration.

15. The method of claim 1, wherein the vector is comprised in a pharmaceutical composition.

* * * * *